United States Patent
Agrawal et al.

(10) Patent No.: US 8,085,898 B2
(45) Date of Patent: Dec. 27, 2011

(54) APPARATUS FOR BONE DENSITY ASSESSMENT AND MONITORING

(75) Inventors: Neeraj Agrawal, Rancho Palos Verdes, CA (US); Manoocher Mansouri Aliabadi, Studio City, CA (US); Christian Wulff, Torrance, CA (US); Kahn-Tze Andrew Lim, El Monte, CA (US)

(73) Assignee: Osteometer Meditech, Inc., Hawthorne, CA (US)

( * ) Notice: Subject to any disclaimer, the term of this patent is extended or adjusted under 35 U.S.C. 154(b) by 145 days.

(21) Appl. No.: 12/463,325

(22) Filed: May 8, 2009

(65) Prior Publication Data
US 2010/0284515 A1    Nov. 11, 2010

(51) Int. Cl.
*G01N 15/02*    (2006.01)
(52) U.S. Cl. .......................................... 378/55; 378/208
(58) Field of Classification Search ............... 378/55, 378/208, 147, 54, 51, 53
See application file for complete search history.

(56) References Cited

U.S. PATENT DOCUMENTS

| | | | |
|---|---|---|---|
| 2,668,912 A * | 2/1954 | Goldfield et al. ............ 378/190 |
| 4,626,688 A | 12/1986 | Barnes |
| 4,774,959 A | 10/1988 | Palmer et al. |
| 4,913,157 A | 4/1990 | Pratt et al. |
| 5,042,489 A | 8/1991 | Wiener et al. |
| 5,119,820 A | 6/1992 | Rossman et al. |
| 5,138,167 A | 8/1992 | Barnes |
| 5,218,963 A | 6/1993 | Mazess |
| RE34,511 E | 1/1994 | O'Neil et al. |
| 5,287,546 A | 2/1994 | Tesic et al. |
| 5,291,537 A | 3/1994 | Mazess |
| 5,353,797 A | 10/1994 | Matsushima et al. |
| 5,432,834 A | 7/1995 | Gershmann |
| 5,603,325 A | 2/1997 | Mazess et al. |
| 5,838,765 A | 11/1998 | Gershman et al. |
| 5,840,029 A | 11/1998 | Mazess et al. |
| 5,841,832 A | 11/1998 | Mazess et al. |
| 6,058,157 A | 5/2000 | Christiansen et al. |
| 6,086,538 A | 7/2000 | Jorgensen et al. |
| 6,320,931 B1 * | 11/2001 | Arnold ............................ 378/56 |
| 6,411,729 B1 | 6/2002 | Grunkin |
| 6,438,201 B1 * | 8/2002 | Mazess et al. ................... 378/56 |
| 6,442,287 B1 | 8/2002 | Jiang et al. |
| 6,690,761 B2 | 2/2004 | Lang et al. |
| 6,811,310 B2 | 11/2004 | Lang et al. |
| 6,853,741 B1 | 2/2005 | Ruth et al. |
| 7,057,254 B2 | 6/2006 | Bui et al. |
| 7,069,066 B2 | 6/2006 | Zeller et al. |
| 7,120,225 B2 | 10/2006 | Lang et al. |

(Continued)

FOREIGN PATENT DOCUMENTS

WO    PCT/US2009/065125    11/2010

*Primary Examiner* — Hoon Song
(74) *Attorney, Agent, or Firm* — Novel IP

(57) ABSTRACT

The present invention relates to a dual energy X-ray apparatus and method for osteoporosis assessment and monitoring. The present invention takes a bone densitometry reading of a patient's wrist to assess osteoporosis and monitor bone loss condition by repeat measurements along with therapy. The bone densitometry system has an X-ray source, dual energy detectors, an arm-rest to place the patient's arm, a motion system to move the source-detector gantry along the patient's forearm, and a computer with a database to archive the wrist image, calculate the bone mineral density, maintain a history of patient information, and generate patient history reports.

13 Claims, 36 Drawing Sheets

U.S. PATENT DOCUMENTS

| | | |
|---|---|---|
| 7,174,000 B2 | 2/2007 | Fehre et al. |
| 2001/0048732 A1 | 12/2001 | Wilson et al. |
| 2003/0052276 A1 | 3/2003 | Francke et al. |
| 2003/0068014 A1* | 4/2003 | Ahn .............................. 378/208 |
| 2005/0015002 A1 | 1/2005 | Dixon et al. |
| 2005/0281478 A1 | 12/2005 | Kaufman et al. |
| 2006/0072703 A1 | 4/2006 | Naidu et al. |

* cited by examiner

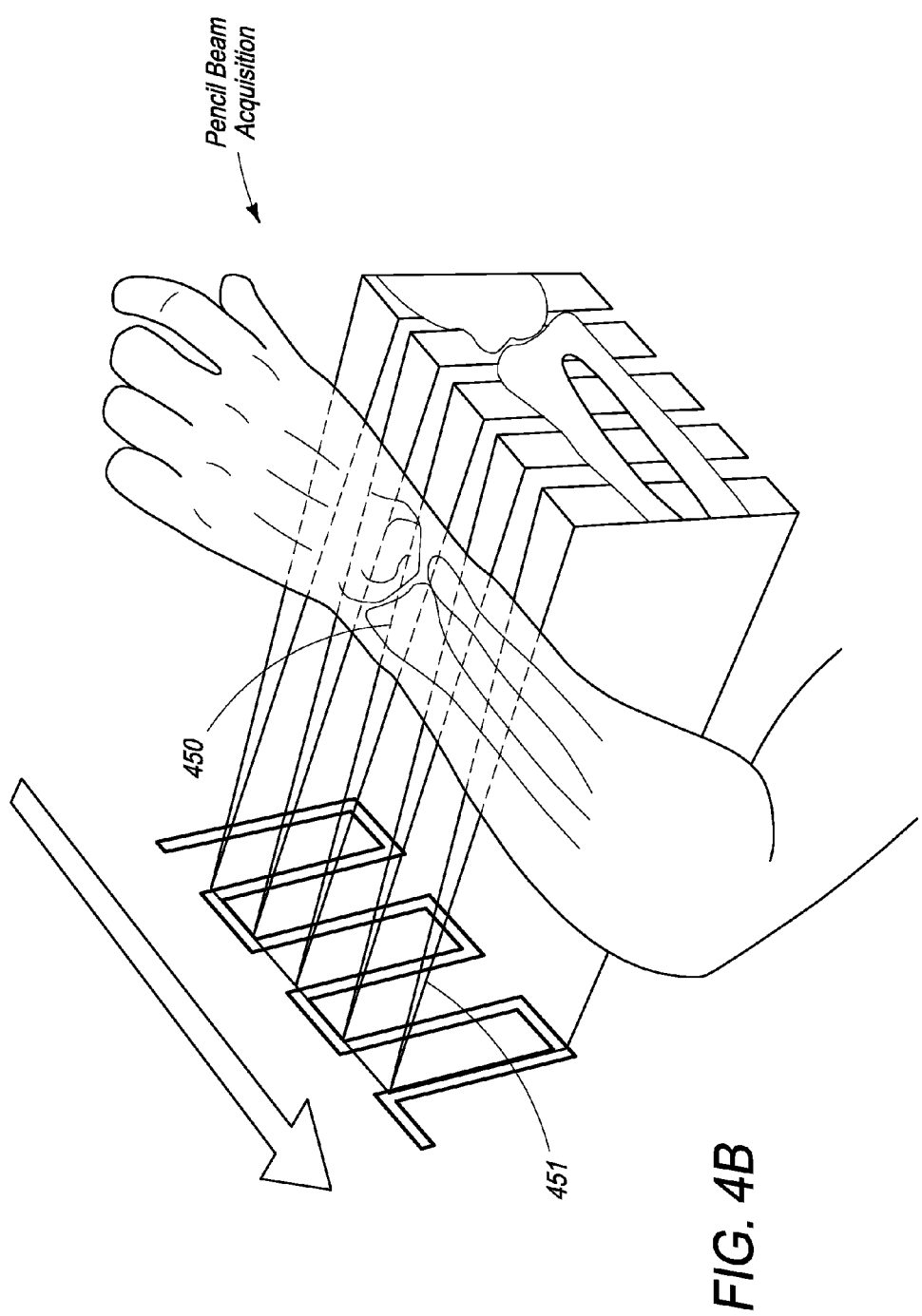

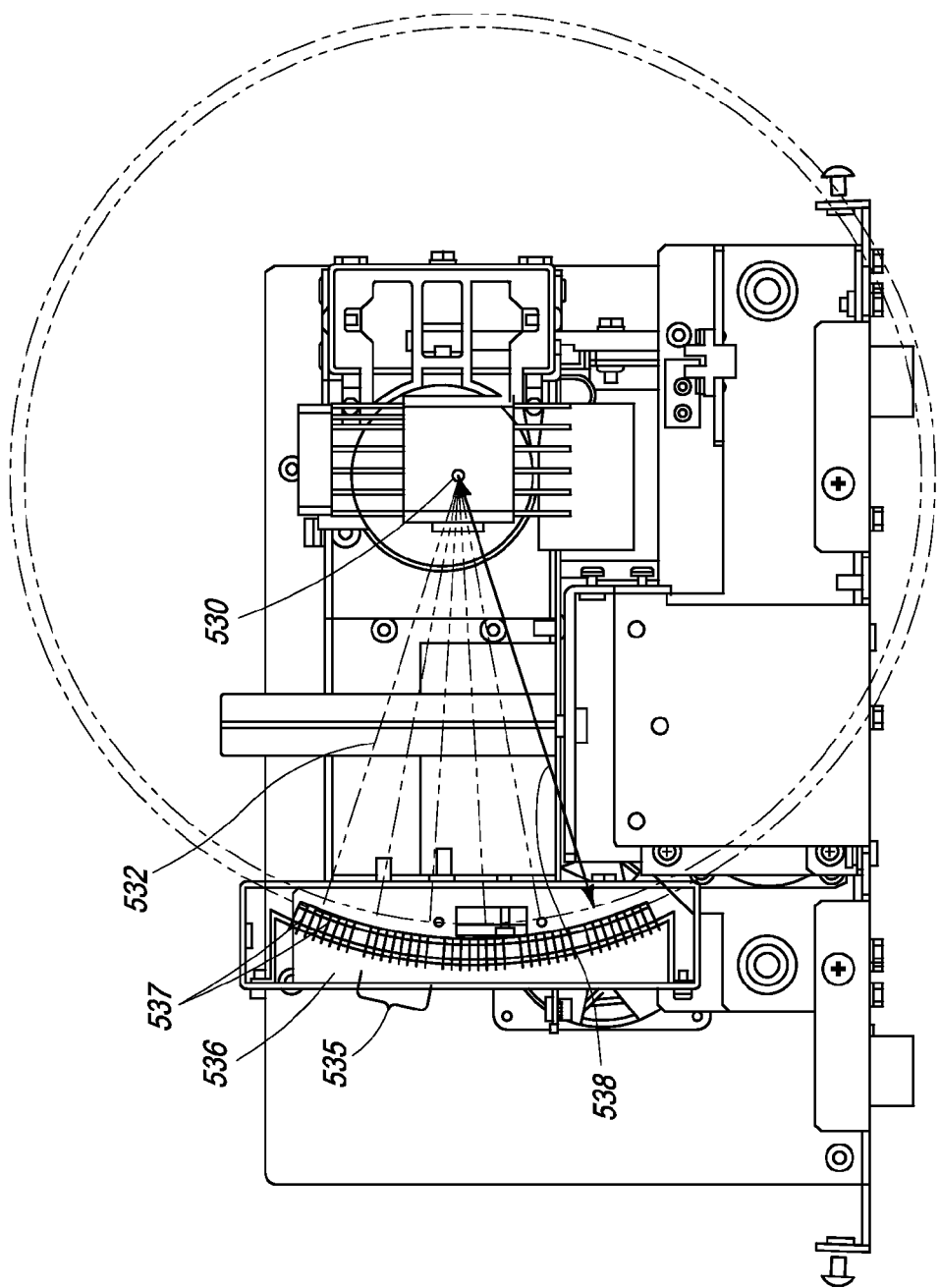

APPARATUS FOR BONE DENSITY ASSESSMENT AND MONITORING

FIELD OF THE INVENTION

The present invention relates to X-ray systems used for medical diagnostics. More particularly, the present invention relates to an X-ray apparatus used for measurement of bone density for assessment and monitoring of bone loss related conditions such as osteoporosis.

BACKGROUND OF THE INVENTION

X-ray systems are used for medical, industrial and security inspection purposes because they can cost-effectively generate images of internal spaces not visible to the human eye. Materials exposed to X-ray radiation absorb the radiation differently and, therefore, attenuate an X-ray beam to varying degrees, resulting in a transmitted level of radiation that is characteristic of the material. The attenuated radiation can be used to generate a useful depiction of the contents of the irradiated object. The absorption of X-rays is measured by detectors after the beam has passed through the object and an image is produced of its contents and presented to an operator. An example of X-ray systems used in medical applications is for osteoporosis assessment and monitoring.

Osteoporosis is a disease of unknown cause which afflicts people, women more often than men, generally as they age. Osteoporosis, or porous bone, is a disease characterized by low bone mass and structural deterioration of bone tissue, leading to bone fragility and an increased susceptibility to fractures, especially of the hip, spine and wrist, although any bone can be affected. After a person reaches peak bone mass, the balance between bone loss and bone formation might start to change. In midlife, bone loss usually speeds up in both men and women. For most women, bone loss increases after menopause, when estrogen levels drop sharply. In fact, in the five to seven years after menopause, women can lose up to 20 percent or more of their bone density.

Bones are composed of both corticular (compact bone) and trabecular (connective strands) bone, where in most areas of trabecular bone, the trabecular mass is surrounded by a relatively thin layer of cortical bone, which may vary in thickness depending upon the individual. High-stress regions of bone tend to be more in cortical bone. Osteoporosis affects trabecular bone more than corticular bone, and is characterized by an absolute decrease in bone tissue mass. Although not common, Secondary Osteoporosis has been termed for bone loss conditions in which the underlying causes of bone loss are typically excessive steroid use, alcoholism, or a sedentary lifestyle.

Conventionally, osteoporosis is diagnosed by conducting a bone mineral density (BMD) test (also referred to as "bone mass measurement") in areas of the bone rich in trabecular bone. A lower reading of bone mineral density implies a greater risk of having a fracture. A BMD test is conducted for multiple reasons such as, to detect low bone density before a person breaks a bone, to predict a person's chances of breaking a bone in future, to confirm a diagnosis of osteoporosis when a person has already broken a bone, to determine whether a person's bone density is increasing, decreasing or remaining stable, and to monitor a person's response to treatment.

BMD test results are provided as a number termed as T-score, which indicates a measure of a person's bone density being above or below normal. FIG. 1A is a pictorial representation 101 of T-scores. As illustrated in FIG. 1A a T-score between +1 and −1 indicates normal bone density, a T-score between −1 and −2.5 indicates low bone density or osteopenia, and a T-score of −2.5 or lower is indicative of osteoporosis. BMD test results also include a Z-score which is used to compare a person's bone density to a normal bone density of a person of the same age and body size. A Z-score above −1.5 is typically normal. Z-scores are used mainly in younger people and children for comparison of the BMD result to other patients of the same age, gender, body size, and ethnic background and typically not used for diagnosis of osteoporosis. Applicant has invented treatment methodologies related to the measurement and use of BMD tests, which are embodied in U.S. patent application Ser. No. 10/623,466, entitled "Integrated Protocol for Diagnosis, Treatment, and Prevention of Bone Mass Degradation", filed on Jul. 18, 2003, and herein incorporated by reference.

Bone density testing can be performed on different bones of a human body, including hip, spine, wrist, finger or heel. There are two basic methods of measuring bone density, one method utilizes X-rays and other method utilizes ultrasound waves. In one method, dual energy X-rays are used to simultaneously obtain two distinct images that represent different X-ray energy spectrum. These two distinct images are then analyzed to separate soft tissue from bone and provide a bone density measurement. Examples of bone density test techniques include hip and spine dual energy x-ray absorptiometry (Central DXA), peripheral dual energy x-ray absorptiometry (pDXA), quantitative ultrasound (QUS), quantitative computed tomography (QCT), and peripheral quantitative computed tomography (pQCT).

While ultrasound methods for determining bone loss condition have been employed in the past, clinical results have shown that they are not adequately accurate. For example, U.S. Pat. No. 6,086,538, assigned to Osteometer Meditech, Inc. and herein incorporated by reference, describes "[a] method of evaluating the status of bone tissue comprising measuring a characteristic of ultrasound transmission through a selected bone at a number of locations using a movable ultrasound transducer which is scanned over a body part containing said bone tissue so as to make said measurements at locations within an area at a spacing between measurement locations of no more than 5 mm, deriving from said measurements information regarding the location of a selected internal anatomical feature of the selected bone, and evaluating said bone tissue status based on ultrasound measurements which reflect said bone tissue status made at a location spatially defined with reference to said internal anatomical feature of the selected bone."

Another prior art method for whole body BMD measurement uses a fan beam X-ray apparatus. For example, U.S. Pat. No. 5,838,765, assigned to Hologic and herein incorporated by reference, describes "[a] whole body x-ray bone densitometry system comprising: a table extending parallel to a Y-axis of an XYZ coordinate system for supporting a patient at a patient position; an x-ray source for emitting a narrow angle fan beam of x-rays to irradiate at any one time a scan line which is transverse to the Y-axis and is substantially shorter than the width of a body cross-section of a typical adult patient occupying the patient position; an x-ray detector aligned with said source along a source-detector axis which is transverse to the Y-axis, for receiving x-rays from the source within the angle of said fan beam after passage thereof through the patient position, said detector comprising a number of detecting elements arranged along a direction transverse to the Y-axis and to the source-detector axis; a source-detector support on which the source and detector are mounted at opposite sides of the patient position; and a scanning mechanism moving the patient table and the source-detector support relative to each other parallel to the Y-axis to scan the patient position with said narrow angle fan beam in successive scans parallel to the Y-axis in which the source-detector axis is at different angles relative to the patient position as between different ones of said successive scans, but in each of said successive scans an origin of the fan beam in the source is at the same vertical distance from the patient table." The accuracy of the method, however, depends on correct patient positioning which may be inconvenient to the patient and also requires successive scans, increasing the patient's radiation exposure.

Yet another prior art method employs a Quantitative Computed Tomography (QCT) X-ray scanning technique where a three dimensional image of the skeletal region is produced and a determination of BMD can be made. For example, U.S. Pat. No. 7,174,000, assigned to Siemens Aktiengesellschaft and herein incorporated by reference, describes "[a] method for measuring a three-dimensional density distribution in a bone, comprising the steps of: disposing a bone to be measured in a region of a rotational axis of a measurement arrangement having an x-ray source and a two-dimensional radiation detector, disposed substantially opposite said x-ray source, rotatable around said rotational axis; irradiating a volume, comprised of voxels, of said bone with x-rays from said x-ray source while rotating said measurement arrangement around said rotational axis through an angle between 180° and 300°, and detecting, with said radiation detector, x-rays attenuated by said bone at a plurality of rotational angles of said measurement arrangement; at each of said rotational angles, and for each voxel, electronically calculating a density value dependent on said attenuated x-rays; and from said density values, electronically calculating an image of said volume representing a density distribution in said bone in said volume." QCT techniques, however, have challenges in performing repeat clinical measurements, have higher radiation dose per scan to the patient, require long patient positioning time, and are a relatively high cost apparatus.

The above-mentioned conventional Bone Density Measurement systems, including quantitative computed tomography (QCT), hip and spine dual energy x-ray absorptiometry (Central DXA), and peripheral quantitative computed tomography (pQCT), require multiple scans in different angular positions to gather image information necessary to determine bone density. This requires longer patient scan time, requires patients to maintain a still body position for a longer duration of time and exposes patients to higher radiation dose. Maintaining a still position for long durations of time becomes difficult for patients and leads to erroneous readings and repeat scans. In addition, prior art systems tend to be large, bulky, difficult to move, and require large amounts of power.

Thus, what is needed is a bone density measurement system that involves a shorter patient observation/scan time; minimizes X-ray exposure to the patient; minimizes movement of the patient during the test; minimizes the effect of patient motion by gathering dual energy X-ray (High Energy and Low Energy) information close in time to each other; is light weight and portable; can be operated remotely and wirelessly for reducing clutter around the scanning apparatus; and supports a multilingual apparatus interface support, so that the system can be easily operated in various countries.

In addition, there is a need for a BDM system that is compatible with Digital Imaging and Communications in Medicine (DICOM) standards to allow for secure distribution and viewing of patient records.

Thus, there is a need for being able to accurately and reliably measure a patient's bone density and to correlate the results of similar tests on a large number of men and women of different ages so as to gain information on whether the patient is at increased risk of fracture.

There is also a need for being able to accurately and reliably measure a patient's bone density and to correlate the results of historical and future similar measurements on the same patient to monitor the bone density of the same patient.

In addition, there is a need for a BMD measurement system that is capable of housing a database with search and report generation capability that can archive all patient scan information.

These requirements indicate a need to both be able to repeat the measurement reliably on the same patient at different times and to make the measurements on many different patients in a consistent manner.

Consequently there is need for a BMD measurement apparatus and method that provides accurate reading and entails a short patient observation time, offers minimal X-ray exposure to the patient and minimizes a need for repositioning the patient.

In addition, a region of interest (ROI) is required to be defined in the patient's bones in trabecular bone rich areas, such that the ROI is consistently locatable at each patient measurement event.

Thus, there is also a need for a BMD measurement apparatus and method that provides high resolution images by using detectors having small lateral dimensions spaced closely together which images finer details of the bone and provides sharper edges for accurate, automatic and repeatable determination of the Region of Interest. Also, since the detectors are directly exposed to radiation during each patient scan, the detectors are susceptible to radiation damage. Hence, there is also a need to include in the apparatus, small sized detectors that provide reduced susceptibility to radiation damage and hence more consistent results over time.

SUMMARY OF THE INVENTION

It is an object of the present invention to provide for a dual energy X-ray apparatus for bone density loss assessment and monitoring whereby a bone densitometry reading of a patient's wrist is taken using the dual energy X-ray apparatus in order to assess bone loss condition. In another object of the present invention, progression of osteoporosis is monitored by taking repeated readings of the patient's wrist over a period of time along, while the patient is undergoing therapy.

In one embodiment, the present invention is an X-ray apparatus for measuring a patient's bone density, comprising: a gantry having a base, a first end, and a second end, further comprising: a radiation source configured to direct radiation through said first end, wherein said radiation source comprises a mono-energetic generator producing radiation at a first energy, and a dual energy detector array located in said second end, comprising at least one detector element pair which comprises at least one high energy detector element and at least one low energy detector element; an armrest area, further comprising a holding bar, for positioning a patient's forearm in the apparatus wherein said armrest area is positioned between said first end and said second end; and a computing system, further comprising a monitor having a display, wherein said display further comprises a graphical user interface (GUI) for controlling said apparatus. In one embodiment, the first energy is 55 KeV and has a current of 0.3 mA.

In one embodiment, the radiation source is collimated to provide a pencil beam of X-rays. In another embodiment, the radiation source is collimated to provide a fan beam of X-rays.

In one embodiment, the at least one detector element pair comprises a low energy detector element and a high energy detector element arranged in a side-by-flip side configuration. Further, the side-by-flip side configuration comprises a low energy detector element, having a top side and a back side, and a high energy detector element, having a top side and a back side, placed adjacent to each other wherein the low energy detector element is placed with its top side up and wherein the high energy element is placed with its back side up.

In one embodiment, the at least one detector element pair comprises a low energy detector element and a high energy detector element arranged in a post-collimated stack configuration. Further, the post-collimated stack configuration comprises: a low energy detector element; a copper strip placed underneath the low energy detector element; a high energy detector element positioned underneath the copper strip; and at least one lead piece for post-collimation, positioned adjacent to the high energy detector element, to eliminate scatter radiation from entering into the high energy detector.

In one embodiment, the gantry of the present invention is capable of moving both horizontally and vertically. Further, in one embodiment, the apparatus comprises at least one optical sensor for detecting the position of the gantry. In one embodiment, the gantry is pivotably attached to a housing and wherein the pivotable attachment permits the first end and second end of the gantry to move in an angular motion around the armrest area.

In one embodiment, the present invention is a method for using an X-ray system for measuring a patient's bone density, having a radiation source, a dual energy detector array, an armrest area, wherein said armrest area further comprises a holding bar, a computing system comprising a monitor having a display, and a gantry comprising said dual energy detector array on a first end and a second end aligned with said first end and configured to emit radiation from said radiation source, comprising the steps of: calibrating the system using a quality control scan of a phantom forearm; entering at least one patient parameter; placing a patient's arm in the armrest and placing a patient's fist around the holding bar; scanning the patient's arm whereby said scanning occurs by: moving said first end and said second end of the gantry around said patient's arm, wherein said arm remains stationary in said armrest and wherein said first end and said second end remain in alignment, emitting radiation from said second end; and detecting radiation in said first end; and generating a bone mass density report based on said detected radiation.

In one embodiment, the method optionally comprises the step of selecting a patient arm, wherein the selection includes either the dominant or non-dominant patient arm. In one embodiment, the method optionally comprises the step of selecting a scan speed.

In one embodiment, the at least one patient parameter includes at least one of a first name, a last name, an address, a unique patient identification code, age, weight, height, date of birth, gender, reference group, and medical history. Further, the at least one patient parameter is saved in a database stored in a memory contained in the computing system. In one embodiment, the generated bone mass density report is displayed on a monitor.

In one embodiment, the present invention is an X-ray apparatus for measuring a patient's bone density, comprising: a gantry having a base pivotally attached to a housing, a first end, and a second end, wherein said first end and second end have a first alignment, further comprising: a radiation source configured to direct radiation through said first end, wherein said radiation source comprises a mono-energetic generator producing radiation at a first energy, and a dual energy detector array located in said second end, comprising at least one detector element pair which comprises at least one high energy detector element and at least one low energy detector element; an armrest area, further comprising a holding bar, for positioning a patient's forearm in the apparatus wherein said armrest area is positioned between said first end and said second end; and a computing system, further comprising a monitor having a display, wherein said display further comprises a graphical user interface (GUI) for controlling said apparatus.

In one embodiment, the first end and second end are configured to move in an angular motion around the armrest area while maintaining said first alignment.

In one embodiment, the radiation source is collimated to provide at least one of a pencil beam of X-rays or a fan beam of X-rays through said first end.

BRIEF DESCRIPTION OF THE DRAWINGS

These and other features and advantages of the present invention will be appreciated, as they become better understood by reference to the following Detailed Description when considered in connection with the accompanying drawings, wherein:

FIG. 4B illustrates X-ray scanning of a patient's forearm by using a pencil beam of X-rays;

FIG. 5D is an expanded illustration of a detector arrangement corresponding to a fan beam configuration mode, in accordance with an embodiment of the present invention;

FIG. 11C is a screenshot of an exemplary electronic form that may be used to enter patient information in a database, in accordance with an embodiment of the present invention;

FIG. 11D is a screenshot of an exemplary GUI that may be used to start a scan, in accordance with an embodiment of the present invention;

DETAILED DESCRIPTION OF THE INVENTION

The present invention is directed towards a dual energy X-ray apparatus for bone density loss assessment and monitoring. A bone densitometry reading of a patient's wrist is taken using the dual energy X-ray apparatus in order to assess bone loss condition. Progression of osteoporosis is monitored by taking repeated readings of the patient's wrist over a period of time, while the patient is undergoing therapy.

The following disclosure is provided in order to enable a person having ordinary skill in the art to practice the invention. Exemplary embodiments are provided only for illustrative purposes and various modifications will be readily apparent to persons skilled in the art. The terminology and phraseology used is for the purpose of describing exemplary embodiments and should not be considered limiting. Various modifications to the preferred embodiment, disclosed herein, will be readily apparent to those of ordinary skill in the art and the disclosure set forth herein may be applicable to other embodiments and applications without departing from the spirit and scope of the present invention and the claims hereto appended. Reference will now be made in detail to specific embodiments of the invention. Language used in this specification should not be interpreted as a general disavowal of any one specific embodiment or used to limit the claims beyond the meaning of the terms used therein.

Figure 1A:
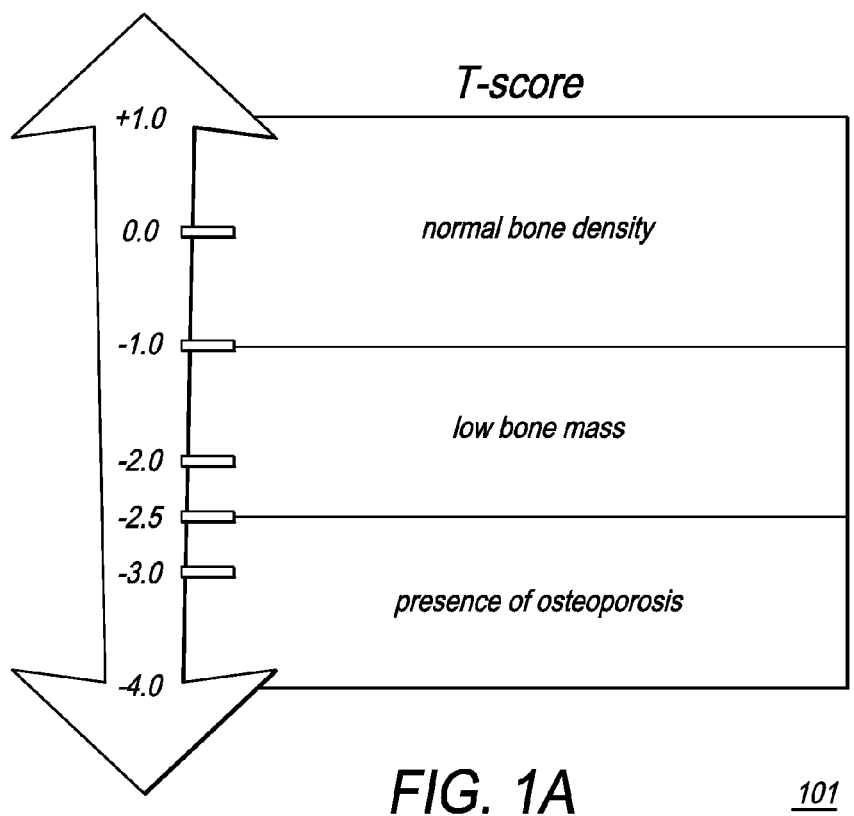
FIG. 1A is a pictorial representation of T-score ranges.
Figure 1B:
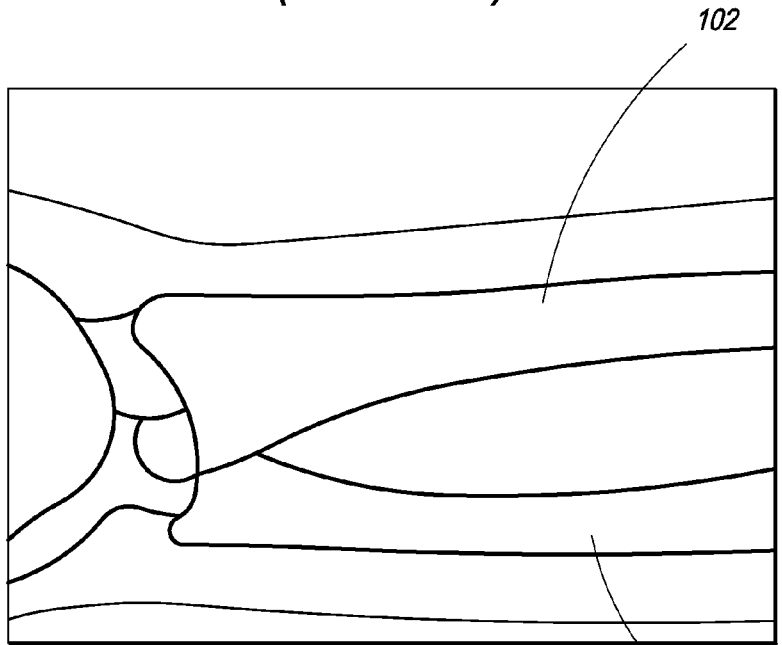
FIG. 1B illustrates a typical X-ray scan of a forearm.
Figure 1D:
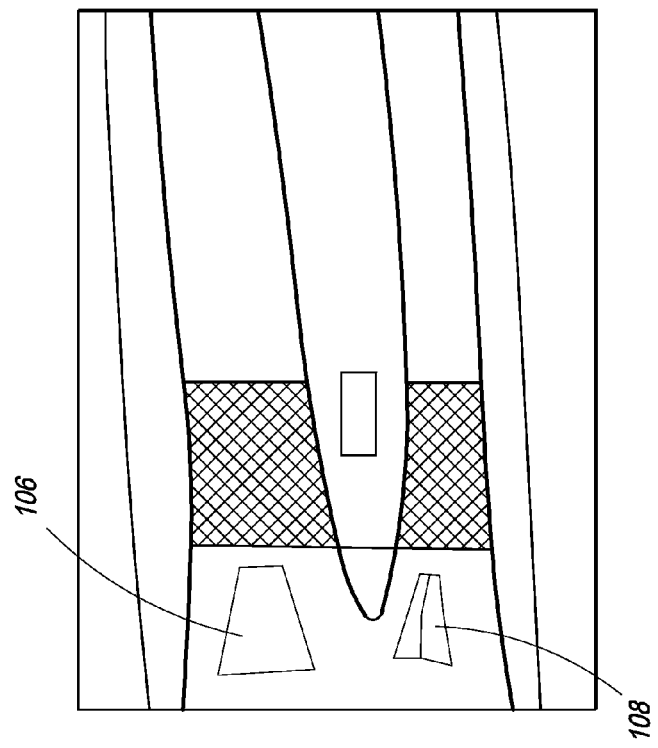
FIG. 1D illustrates trapezoidal regions of interest (ROI) and Distal ROI (DROI) within the radius and ulna of the forearm.
Figure 1C:
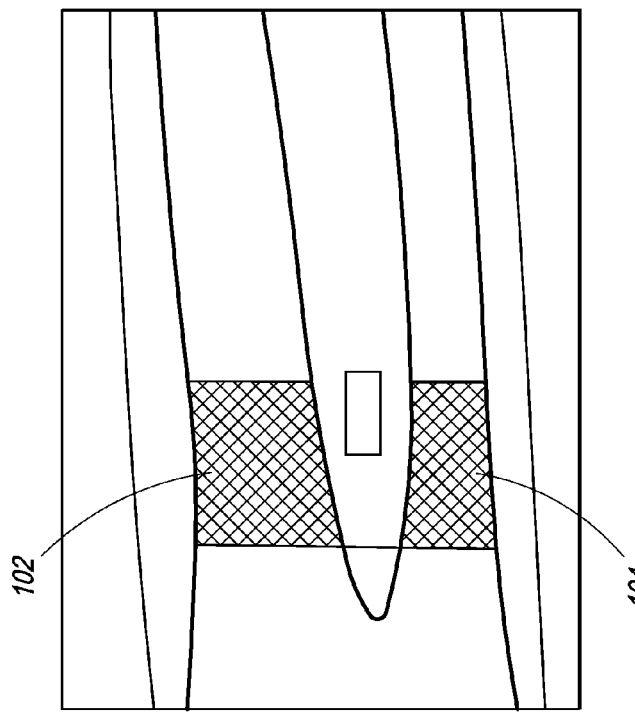
FIG. 1C illustrates a radius and ulna portion of a forearm, detected by an edge detection algorithm.

In one embodiment of the present invention, a Region of Interest (ROI) is defined in order to reliably perform repeat measurements on patients. In an embodiment of the present invention, in order to achieve reliable and repeatable BMD measurements at a wrist area of a patient, a ROI is defined within the radius and ulna of the patient's forearm. The ROI is defined in a manner such that it can be located consistently during each BMD measurement session. FIG. 1B illustrates a typical X-ray scan of a patient's forearm. The X-ray scan shows a patient's forearm, and more specifically, radius 102 and ulna 104. A ROI is defined as a trapezoidal area in the radius 102 and ulna 104 and is positioned close to the end plate of the bone, avoiding the dense cortical area and extending beyond the turning points of the bone. In an embodiment of the present invention, the method of defining the ROI described in U.S. Pat. No. 6,058,157 (the "'157 patent"), assigned to Osteometer Meditech Inc. and incorporated herein by reference, is employed. FIG. 1C illustrates radius 102 and ulna 104 detected by edge detection algorithm as described in U.S. Pat. No. 6,058,157. FIG. 1D illustrates trapezoidal regions of interest within the radius and ulna. Trapezoidal regions of interest 106 and 108 are located in the radius 102 and ulna 104 respectively, by using the method described in the '157 patent. Bone Mineral Density (BMD) is calculated by acquiring data from the trapezoidal areas 106 and 108.

Figure 1E:
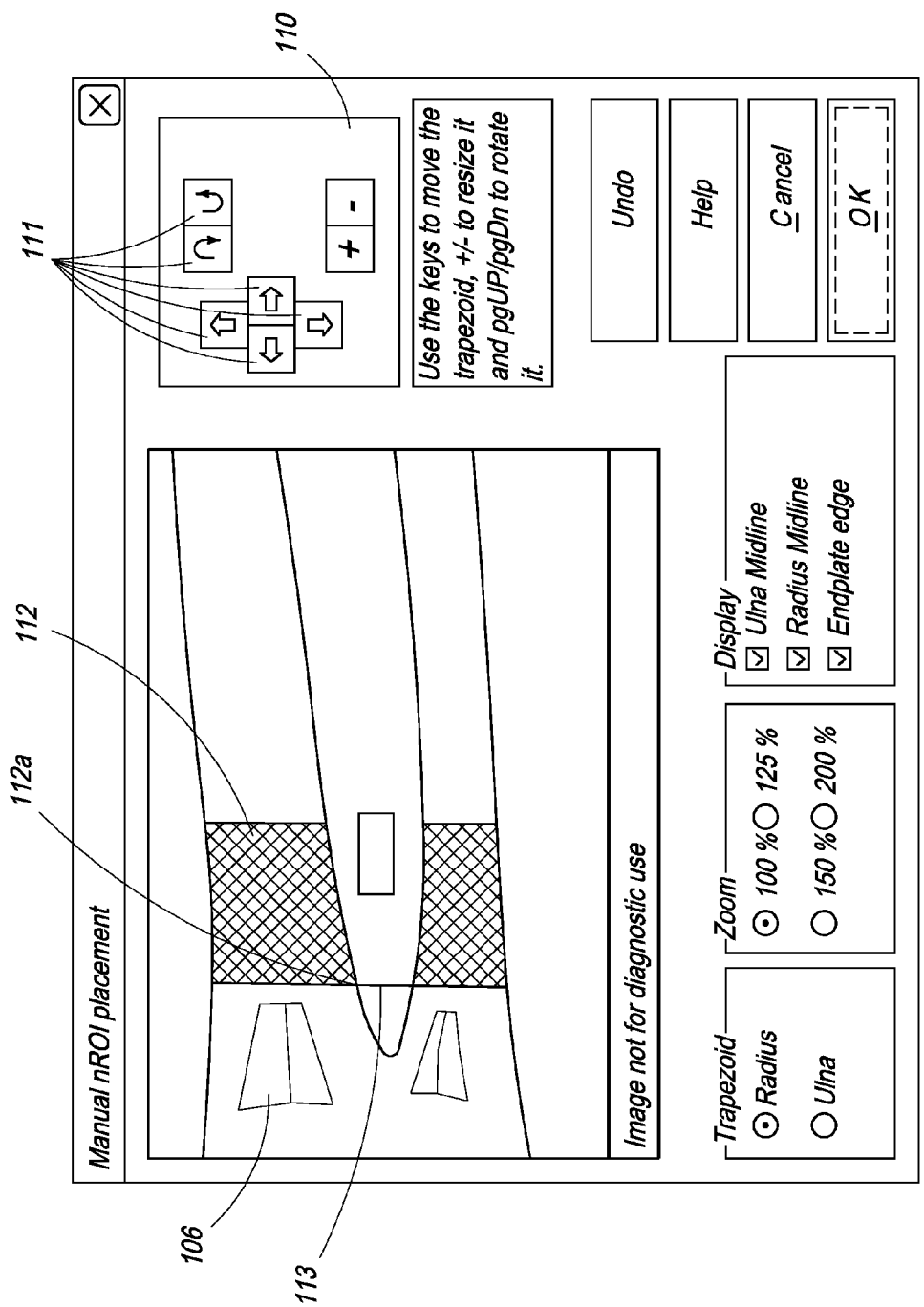
FIG. 1E is a screenshot of an exemplary electronic form that may be used to manually adjust the trapezoidal ROI within the radius and ulna, in accordance with an embodiment of the present invention.

The ROI is typically a trapezoidal area in order to maximize the bone region in the radius and ulna being analyzed without including the dense cortical area of the bone. However, once the automatic selection of trapezoidal ROI area is complete, the system of the present invention allows an operator to manually adjust the ROI by adjusting the edges of the trapezoid. FIG. 1E is a screenshot of an exemplary electronic form that may be used to manually adjust the ROI in the radius and ulna, in accordance with an embodiment of the present invention. The ROI may be manually adjusted by using the arrow buttons 111 provided in region 110, including manual adjustments for horizontal position, vertical position, angular orientation, and size of the trapezoidal region. In addition to the trapezoidal ROI 106, a Distal Region of Interest (DROI) 112 is also defined, where BMD measurement is typically made on a first patient scan to compare with the trapezoidal ROI. In one embodiment, the beginning point 112a of the DROI 112 is defined at the point where the distance 113 between the radius and ulna is in the range of 7 mm to 9 mm, and preferably exactly 8 mm. In one embodiment, the width of the DROI 112 is in the range of 22 to 26 mm, and preferably 24 mm. Both the DROI 112 and trapezoidal ROI are typically used in the first patient scan while subsequent scans on the same patient for BMD measurement are usually performed in the trapezoidal ROI only.

Figure 2A:
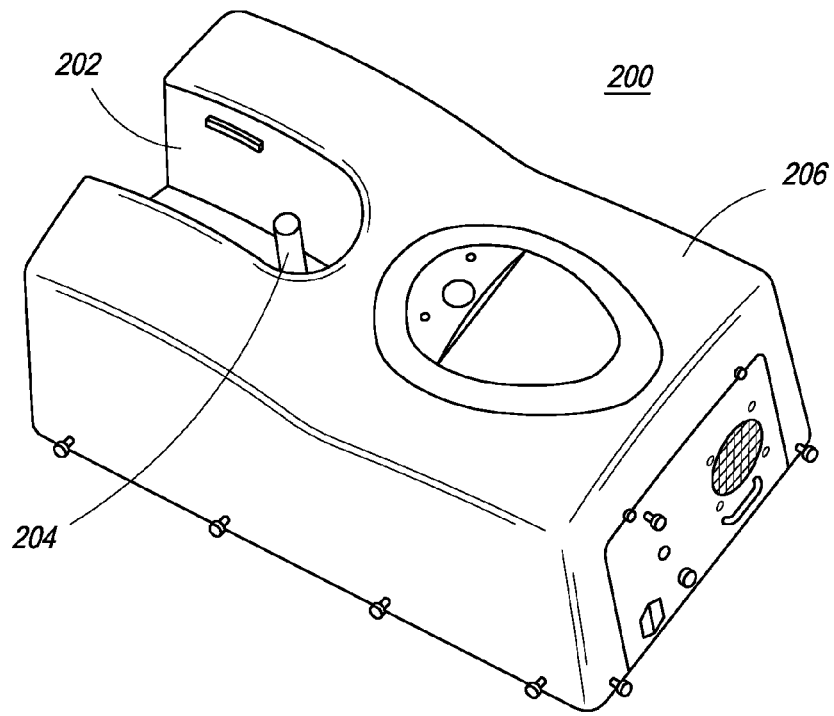
FIG. 2A illustrates an outer view of a dual energy X-ray apparatus with cover, in accordance with an embodiment of the present invention.
Figure 2B:
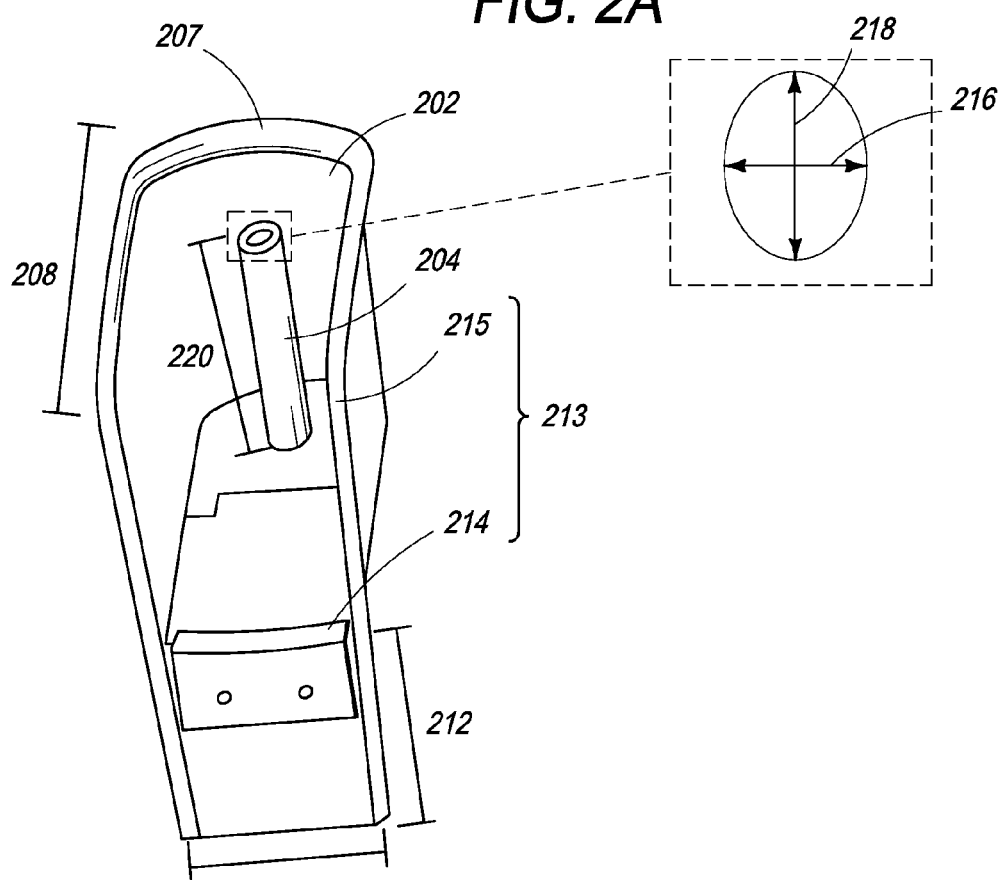
FIG. 2B is a view of an arm-rest comprising a holding bar, in accordance with an embodiment of the present invention.

FIG. 2A illustrates an outer view of a portion of the dual energy X-ray system 200, with cover, in accordance with an embodiment of the present invention. The dual energy X-ray system comprises an arm-rest or arm placement area 202, a holding bar 204 and a cover 206. During a BMD measurement session a patient is required to place a forearm in the arm-rest 202 and form a fist around the holding bar 204. This method of placement of the patient's forearm ensures a consistent scan of the ROI in the wrist area and eliminates the need for repositioning of the forearm. FIG. 2B is a view of the arm-rest area 202 comprising a holding bar 204, in accordance with an embodiment of the present invention. Arm-rest area 202 is U-shaped, with a holding bar 204 placed in the distal end 206 of the dual energy X-ray system of the present invention. The overall length 208 of the armrest area 202 is in the range of 194.8 mm and 292.2 mm, and preferably exactly 243.5 mm. The overall width 210 of the armrest area 202 is in the range of 79.3 mm and 119 mm, and preferably exactly 99.15 mm. Height 212, from the base of the system to the floor or base 214 of armrest area 202 is in the range of 86.4 mm and 129.6 mm, and preferably exactly 108 mm. Height 213, from the base 214 to the top 215 of armrest area 202 is in the range of 136 mm to 210 mm and more preferably, ranges from 170 mm to 175 mm at its highest point. Thus, in one embodiment, the system has an overall height ranging from about 222 mm to 340 mm, but preferably 278 mm to 283 mm. In one embodiment, holding bar 204 has a diameter 216, in the range of 17.6 mm and 26.4 mm, and preferably exactly 22 mm in one area and a diameter 218, in the range of 24 mm and 36 mm, and preferably exactly 30 mm in another area, and is thus not perfectly cylindrical in shape. In one embodiment, holding bar 204 has an approximate height 220 in the range of 100 mm and 150 mm, and preferably exactly 125 mm. In one embodiment, the radius of the armrest is in the range of 39.7 mm and 59.5 mm, and preferably exactly 49.6 mm. In one embodiment, the radius defines the curvature of the back portion 207 of the armrest, closest to the holding bar.

Figure 2C:
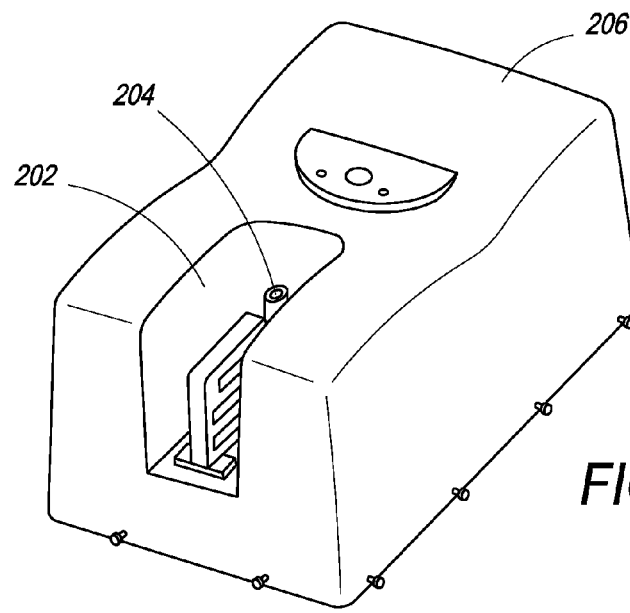
FIG. 2C is another perspective view of an arm-rest comprising a holding bar, in accordance with an embodiment of the present invention.

In another embodiment, as shown in FIG. 2C, armrest area 202 and holding bar 204 are integrated into cover 206.

It should be noted herein that the dual energy X-ray system of the present invention, in one embodiment, further comprises a monitor (not shown) having a display, for displaying the at least one graphical user interface (GUI) of the present invention. In addition, the monitor is employed, as described in greater detail below, to display at least one GUI, further comprising at least one button for controlling the system of the present invention. The monitor can be connected to the X-ray apparatus of the present invention using either wired or wireless connections, as are known to those of ordinary skill in the art. In another embodiment, the monitor may be located either proximate to the X-ray system of the present invention or in a remote location.

It should be noted herein and understood by those of ordinary skill in the art that the graphical user interfaces of the present invention are implemented using a computer program/software application running on a computing system that controls the visual composition and temporal behavior of the GUI and allows the GUI(s) of the present invention to be manipulated using any type of input device, including, but not limited to a mouse, touch screen or keyboard.

Figure 3A:
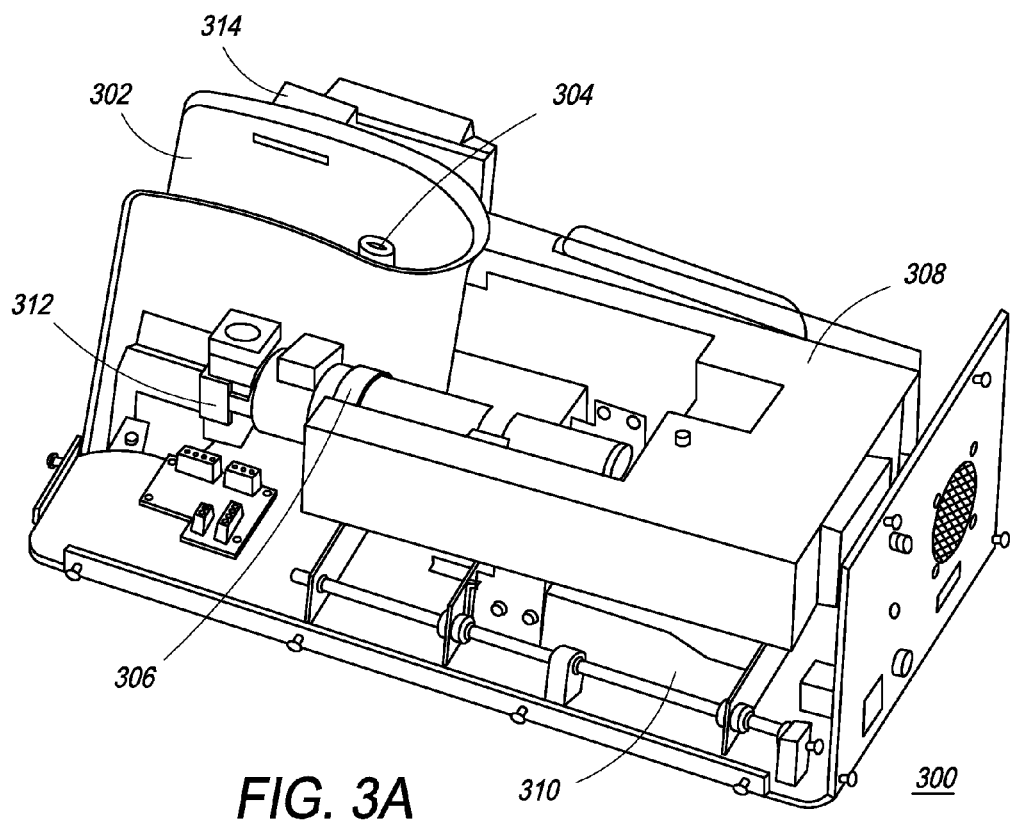
FIG. 3A illustrates an inner view of a dual energy X-ray apparatus, in accordance with an embodiment of the present invention.

FIG. 3A illustrates an inner view of the dual energy X-ray apparatus shown in FIGS. 2A and 2B, in accordance with an embodiment of the present invention. Dual energy X-ray apparatus 300 comprises an arm-rest 302, a holding bar 304, an X-ray tube 306 mounted on a gantry 308, and a motor assembly 310 to move the gantry 308 along with the X-ray tube 306 to scan a patient's forearm, and detector array box 314. In one embodiment, X-ray tube 306 comprises an X-ray source 312. In one embodiment, as shown in FIG. 3A, gantry 308 is positioned behind arm-rest area 302, such that it can be moved in a horizontal and/or angular motion, without requiring re-positioning of the patient arm. The relative movement and positioning of the gantry is described in further detail below with respect to FIGS. 7A, 7B, 7C, and 7D.

Referring back to FIG. 3A, X-ray source 312 and detector array(s) 314 are used to scan and image the wrist area of the patient's forearm (not shown) placed in the arm-rest area 302. In one embodiment, X-ray source 312 is a mono-energetic generator that provides radiation at 55 KeV and 0.3 mA.

Figure 3B:
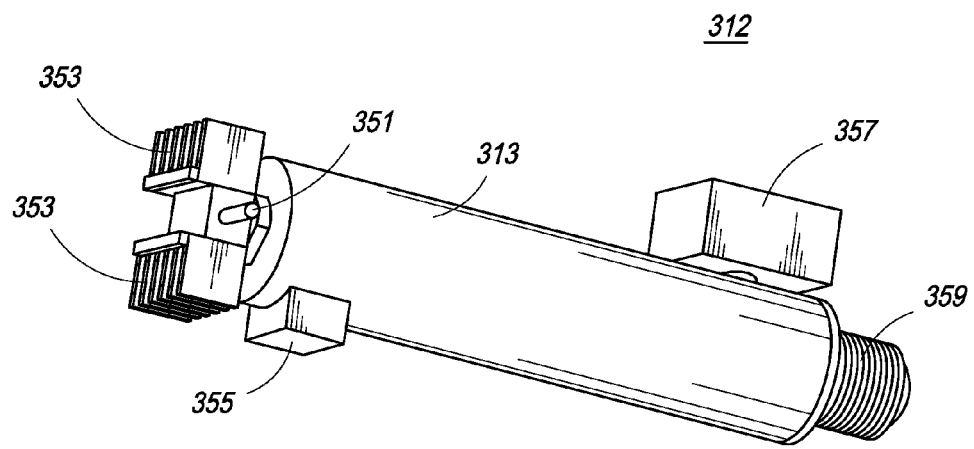
FIG. 3B illustrates an outer view of the X-ray source, in accordance with one embodiment of the present invention.
Figure 3C:
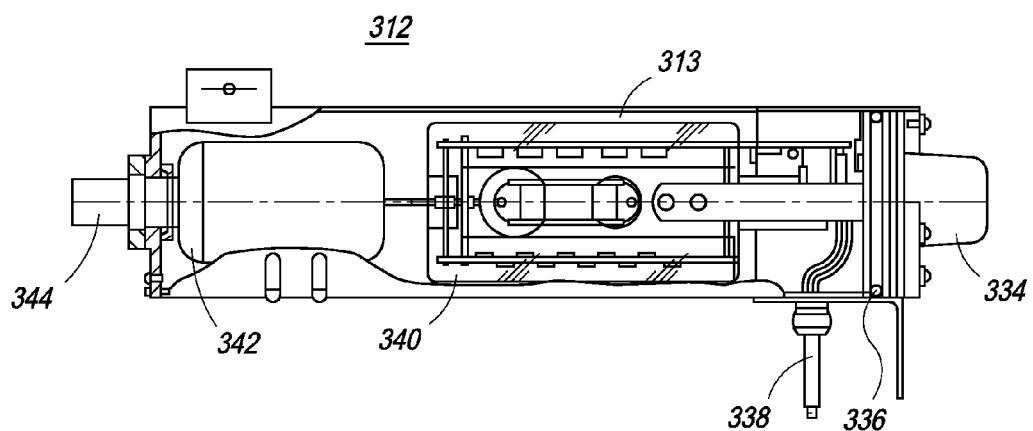
FIG. 3C illustrates an inner view of the X-ray source, in accordance with an embodiment of the present invention.

FIG. 3B illustrates an outer view of the X-ray source 312. In one embodiment, outer shell 313 of X-ray source 312 is cylindrical in shape for ease of mounting and to minimize the volume used in the gantry assembly of the X-ray apparatus. X-ray source 312 further comprises a collimator assembly 351, which can be a collimator assembly for shaping the X-ray beam into either a pencil beam or fan beam of radiation; heat sink fin(s) 353; X-ray source mounting block 355 for mounting the X-ray source to the system of the present invention; high voltage electronics 357; and an expansion chamber/bellows 359 to accommodate heated oil. FIG. 3C illustrates an inner view of the X-ray source 312, showing outer shell 313, expansion bellows 334, an O-ring seal for oil 336, high voltage cable 338, a potted high voltage multiplier assembly 340, an X-ray glass tube 342, and a copper tip 344 for emitting radiation. A collimator (not shown) is placed around the copper tip 344 for shaping the X-ray beam to a pencil beam configuration or a fan beam configuration. The components are packaged within the outer shell 313 in a manner so as to utilize minimal overall volume.

Figure 4A:
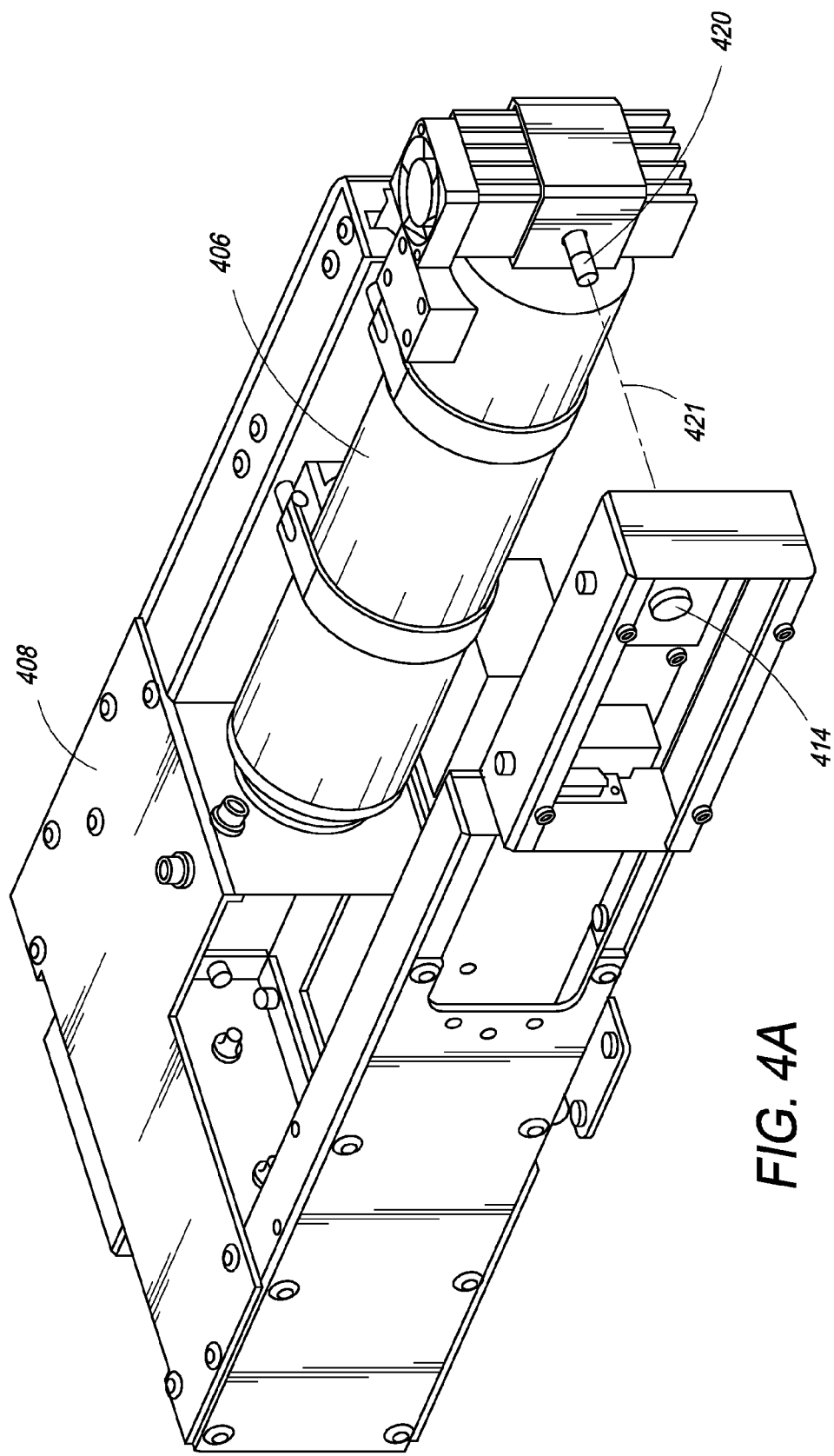
FIG. 4A illustrates a pencil beam X-ray source, in accordance with an embodiment of the present invention.

In one embodiment of the present invention, the X-ray source is collimated to produce a pencil beam of X-rays. FIG. 4A illustrates a pencil beam X-ray source, in accordance with an embodiment of the present invention. The X-ray source 406 produces a beam of radiation (not shown) which is shaped into pencil beam of X-rays 421, by collimator 420, which passes through a patient's forearm and is detected by dual energy detector array 414. FIG. 4B illustrates X-ray scanning of a patient's forearm 450 by using a pencil beam of X-rays 451. In the pencil beam configuration mode both horizontal and angular motions of the source gantry 408 are required in order to generate a scanned image of the patient's forearm, as described in greater detail below.

Figure 4C:
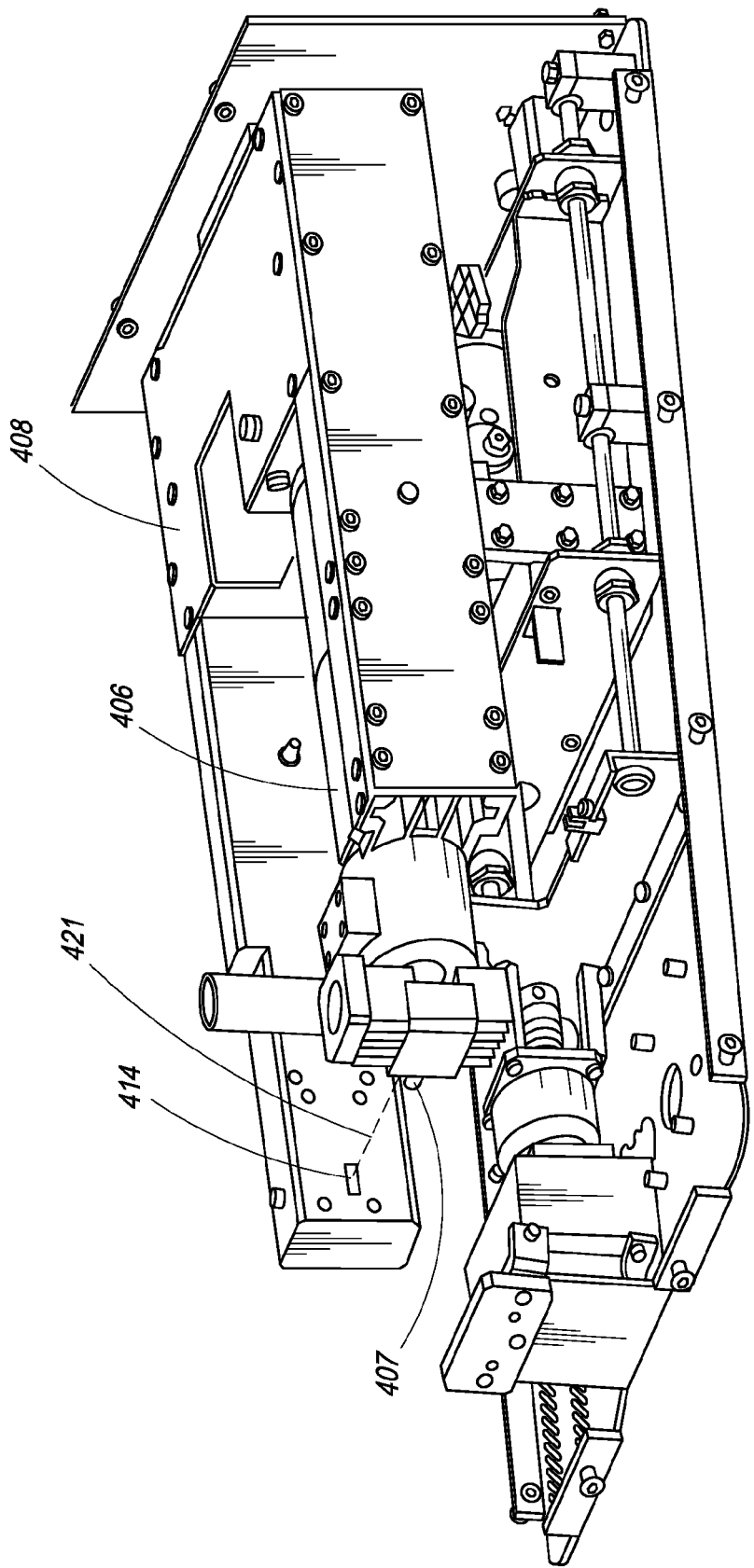
FIG. 4C illustrates a detector arrangement corresponding to a pencil beam configuration mode implemented in one embodiment of the X-ray apparatus of the present invention.

FIG. 4C illustrates a detector arrangement corresponding to a pencil beam configuration mode implemented in one embodiment of the X-ray apparatus of the present invention. As shown in FIG. 4C, the detector array 414 is positioned directly across from X-ray source 406, at the point where pencil beam of X-rays 421 exits the aperture 407 of the X-ray source 406. Because both detector array 414 and source 406 are located on the same movable gantry 408, there is no need for alignment.

Two methods have conventionally been used to carry out dual energy X-ray imaging. One method approximates dual energy X-rays using voltage switched X-ray tubes. Switching x-ray tube voltage at high frequencies can be technically complex and also makes the data acquisition time longer to wait for the X-ray switching to occur. Another method uses mono-energetic X-rays and an energy selective detector. A typical configuration of energy selective detector is a solid state overlapped front-back detector with two separate scintillation materials placed in a two-sided configuration. In a typical prior art configuration, both detector elements are in the path of X-rays where the first detector element is more sensitive to the low energy X-rays and the second detector element is more sensitive to the hardened higher energy X-rays which have passed through the first element.

For example, U.S. Pat. No. 4,626,688, assigned to Barnes and incorporated herein by reference, describes "[a]n energy discriminating radiation detector comprising: (a) a first element comprising a first material of a kind which is preferentially responsive to penetrative radiation of a first energy range; (b) a second element comprising a second material different in kind from said first material and of a kind which is preferentially responsive to penetrative radiation of a second energy range extending higher than said first energy range and which is positioned to receive radiation which has penetrated through a portion of said first element; and (c) a filter of penetrative radiation interposed between said first and second elements."

In addition, U.S. Pat. No. 5,138,167, assigned to The University of Alabama, Birmingham and incorporated herein by reference, describes "[a]n energy discriminating radiation detector comprising: a) a first element comprising a first material of a kind which is preferentially responsive to penetrative radiation of a first energy range, said response being defined by a first characteristic, said first characteristic defining a first peak radiation absorptive energy value; b) a second element comprising a second material different from said first material and of a kind which is preferentially responsive to penetrative radiation of a second energy range said response being defined by a second characteristic, said second energy range extending higher than said first energy range, said second characteristic defining a second peak radiation absorptive energy value higher than said first peak energy value, said second element being positioned to receive radiation which has penetrated through a portion of said first element, and c) a filter of penetrative radiation interposed between said first and second elements, said filter comprising material and having thickness such that said filter exhibits a main radiation attenuation roll off with respect to energy, said roll off occurring at an energy value lower than said second peak value."

In addition, some prior art configurations suggest a side-by-side detector arrangement. This arrangement can be disadvantageous as it requires some alignment adjustment, thus potentially causing some motion artifact. In addition, it is more challenging to position a filter in this arrangement.

For example, U.S. Pat. No. 5,841,832, assigned to Lunar Corporation and incorporated herein by reference, describes "[a] dual energy x-ray detector comprising: solid-state low energy x-ray detector elements each detecting incident low energy x-rays along the radiation axis over a predetermined detector area to produce a first electronic signal proportional to the incident high energy x-rays; and solid state high energy detector elements each detecting incident high energy x-rays along the radiation axis over a predetermined detector area to produce a second electronic signal proportional to the incident high energy x-rays; wherein the low and high energy detector elements are separated into side-by-side element rows, the rows displaced in a direction across the radiation axis. Similarly, U.S. Pat. No. 5,841,833, also assigned to Lunar Corporation and incorporated herein by reference, describes "[a] dual energy x-ray detector comprising: low energy solid state x-ray detector elements detecting incident low energy x-ray photons each over a predetermined detector area to produce a first electronic signal proportional to the incident low energy photons; and high energy solid state x-ray detector elements detecting incident high energy x-ray photons each over a predetermined detector area to produce a second electronic signal proportional to the incident high energy photons; wherein the low and high energy x-ray detector elements are arranged in at least one row of alternating high and low energy detector elements" and where the dual energy detector includes "at least two rows and wherein the low and high energy detector elements are also arranged in columns of alternating high and low energy detector elements perpendicular to the rows".

In the detector arrangements described above, it is difficult to position a copper filter above the high energy detector to achieve better energy spectrum separation between low and high energy X-rays. The separation of bone and soft tissue tends to be of poor quality without acceptable separation of low energy and high energy X-rays, thus affecting the accuracy of the BMD calculation. Also, the alternating high and low energy detector arrangement is difficult to practically implement.

Further, since detectors are directly exposed to radiation during each patient scan, the detectors are susceptible to radiation damage which increases detector reverse bias current and increases forward voltage, both of which contribute to degradation of data quality received from the detectors, which in turn, adversely affects the determination of the ROI and the BMD calculation.

Preferred detectors used in the present invention have low crosstalk characteristics and can be packaged in high density arrays. Low crosstalk in the detectors allow low noise in the signal response thereby improving signal-to-noise ratio, which in turn allows a higher quality image to be generated and more accurate BMD results to be calculated. Because the detectors are packaged in highly dense arrays, fine object details can be elucidated, resulting in a high resolution image that allows for accurate and repeatable BMD measurements. Details of exemplary detector arrays are described in U.S. Pat. No. 7,057,254 (the "'254 patent") assigned to OSI Optoelectronics, Inc., which is herein incorporated by reference in its entirety. The detectors described in the '254 patent are generally employed to collect dual energy X-ray data.

Figure 4D:
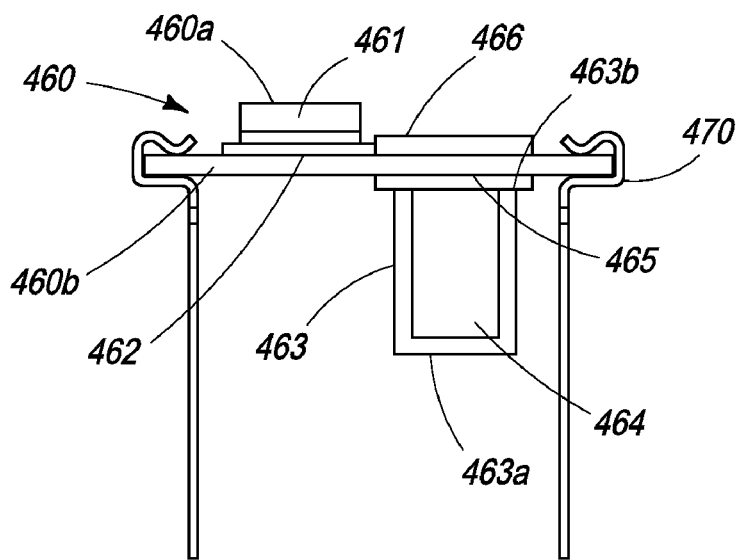
FIG. 4D illustrates a side-by-flip side detector arrangement as used in a pencil beam configuration mode.

The present invention describes a method for acquiring dual energy X-ray data utilizing a novel detector element configuration and arrangement of the detector elements in an array. In one embodiment, the detector elements comprising detector array 414 are arranged in a "side-by-flip-side" configuration. FIG. 4D illustrates a side-by-flip-side detector arrangement as used in pencil beam configuration mode. In one embodiment, the side-by-flip-side detector arrangement comprises a low energy detector element 460, having a top side/front side 460a and a back side 460b further comprising a low energy scintillating material 461 in front side 460a and a low energy photodiode 462 in back side 460b, for detecting low energy X-ray radiation. The back side of the low energy detector element 460b is attached to the top side of a detector holding structure 470.

In one embodiment, the detector array further comprises a high energy detector element 463, having a front side 463a and a back side 463b, further comprising high energy scintillating material 464 and a high energy photodiode 465, respectively, for detecting high energy X-ray radiation. In a side-by-flip-side configuration, low energy detector element 460 and high energy detector element 463 are positioned adjacent to each other, whereby the low energy component 460 is placed with its top side 460a up and its bottom side in physical contact with the top side of the detector holding structure 470 and whereby the high energy component 463 is placed with its back side 463b (i.e. flip side) in physical contact with the bottom side of the detector holding structure 470.

In one embodiment, a copper filter 466 is placed in the beam path of the high energy detector element 463 to attenuate most of the low energy X-ray spectrum allowing the hardened high energy X-ray spectrum to pass through, thereby enhancing the separation of the X-ray energy spectrum detected by the two detector elements. It should be understood by those of ordinary skill in the art that the photodiode elements are placed in a small PCB in an array configuration depending upon the number of photodiode element pairs needed. In a pencil beam configuration, only one detector element pair is used—one low energy detector and one high energy detector, as described above. The copper filter 466 is preferably physically attached to the top side of detector holding structure 470.

Figure 4E:
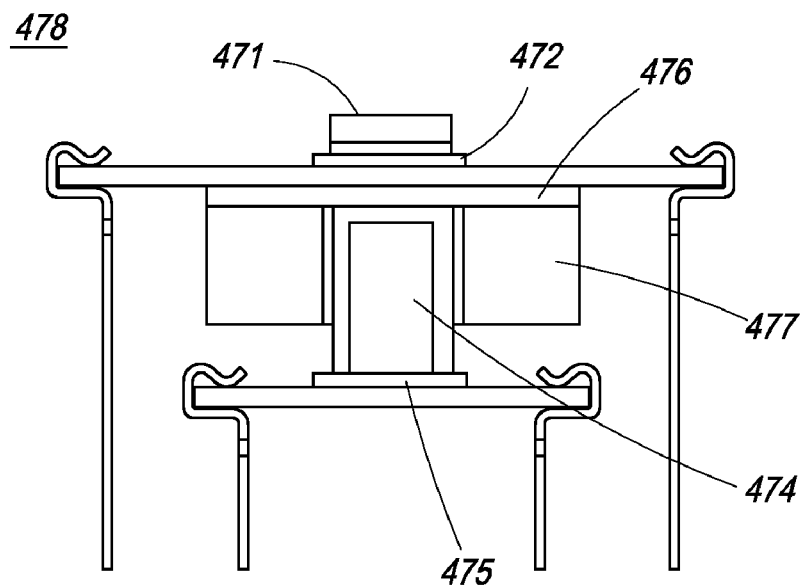
FIG. 4E illustrates a post-collimated stack detector arrangement as used in a pencil beam configuration mode.

In another embodiment, the detector elements comprising detector array 414 are arranged in a post-collimated stack configuration. FIG. 4E illustrates a post-collimated stack detector configuration as used in pencil beam configuration mode of the X-ray apparatus of the present invention. As shown in FIG. 4E, the post-collimated stack detector arrangement 478 comprises a low energy scintillator material 471, placed on top of low energy photodiode 472. A copper strip 476 is placed just underneath the low energy photodiode 472, to aid in filtering and separating the low and high energy X-rays in the energy spectrum. The post-collimated stack detector 478 also comprises a high energy scintillator 474 and a high energy photodiode 475, positioned underneath the copper filter 476. In addition, the post-collimated stacked detector further comprises at least one lead piece 477, positioned adjacent to the high energy detector element for post-collimation to eliminate scatter radiation from entering into the high energy detector. In one embodiment, two lead pieces 477 are employed, one at each side of the high energy detector. Scatter radiation would decrease the signal-to-noise ratio, as the scatter would contribute to noise.

Figure 5A:
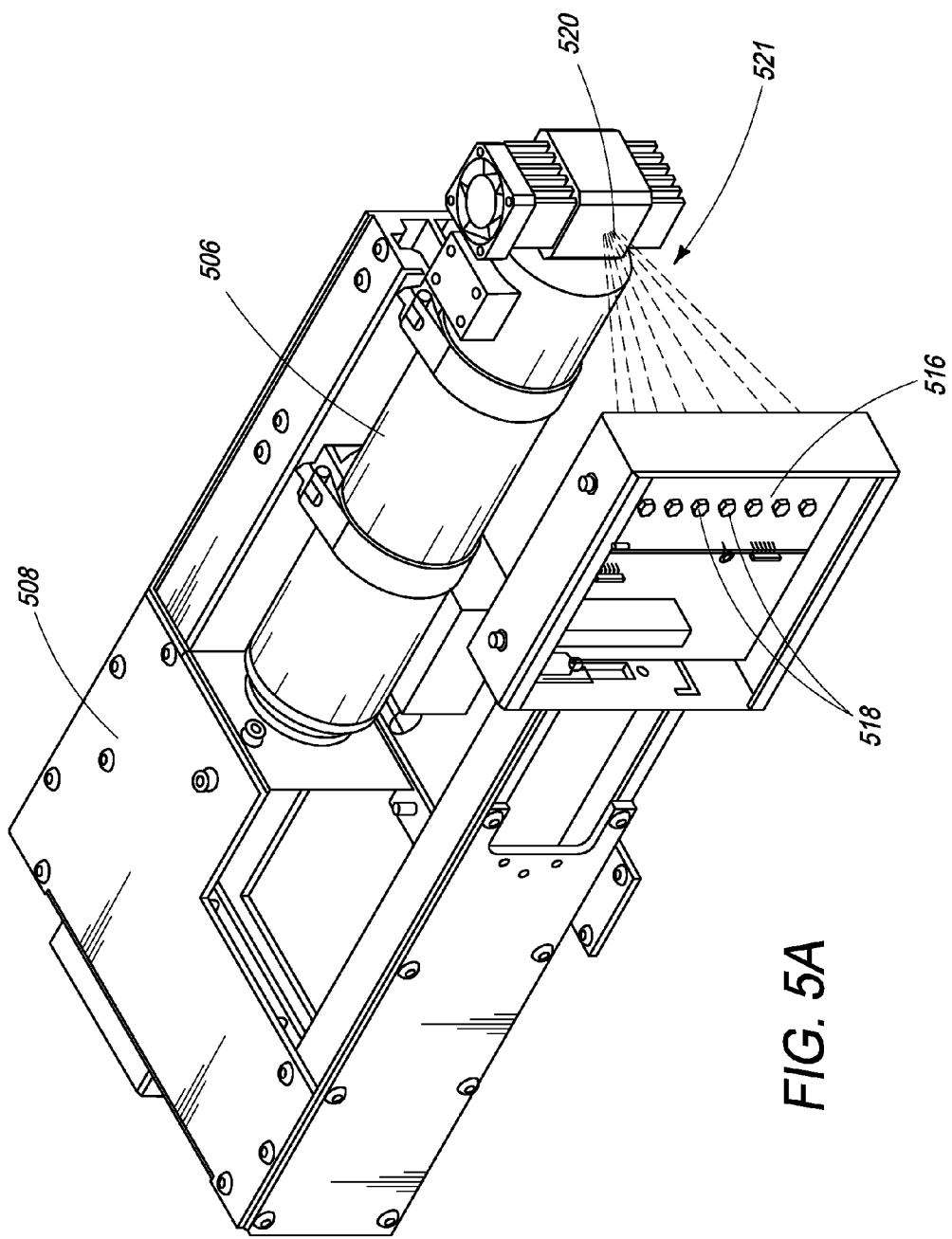
FIG. 5A illustrates a fan beam X-ray source, in accordance with an embodiment of the present invention.
Figure 5B:
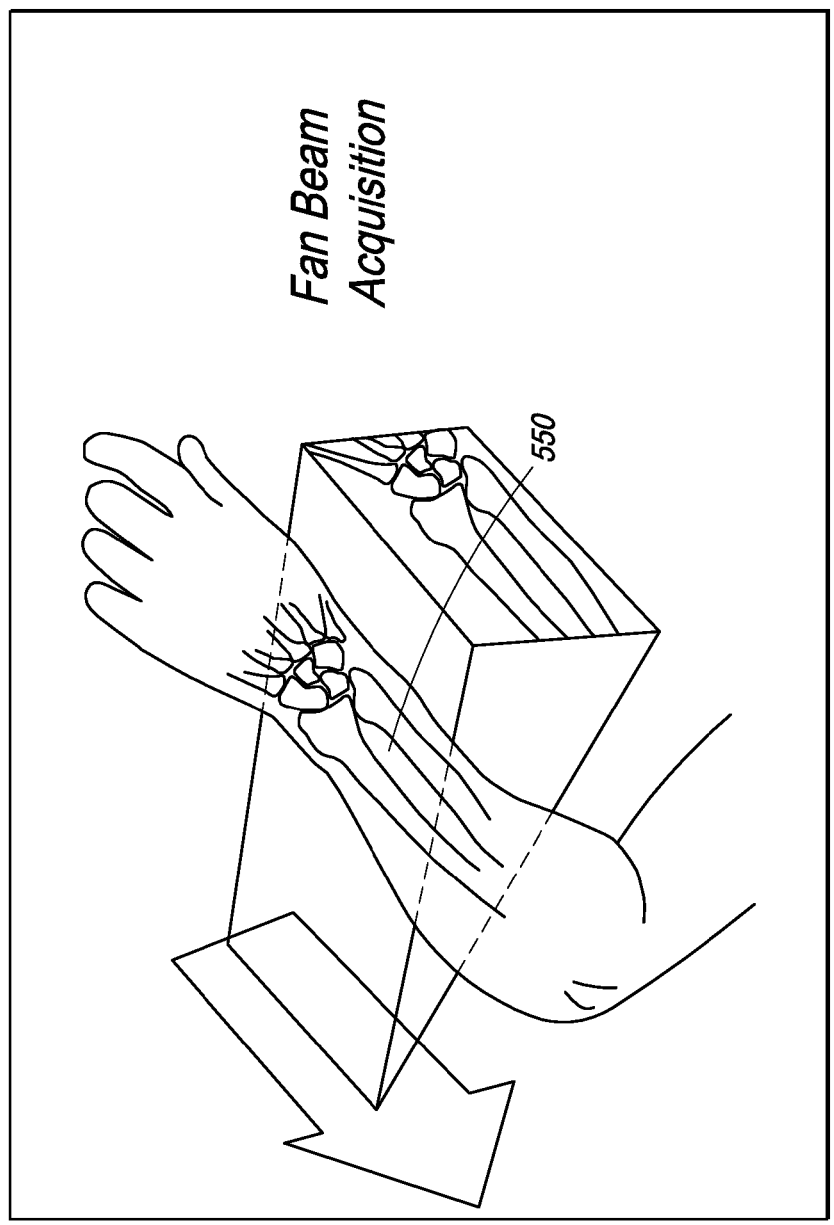
FIG. 5B illustrates X-ray scanning of a patient's forearm by using a fan beam X-ray source.

In another embodiment of the present invention, the X-ray source is collimated to produce a fan beam of X-rays. FIG. 5A illustrates a fan beam X-ray source 506, in accordance with an embodiment of the present invention. The X-ray source collimator 520 shapes radiation emanating from X-ray source 506 into a fan beam of X-rays 521 which passes through a patient's forearm (not shown) and is detected by a detector assembly 516 comprising a plurality of dual energy detectors 518. In the fan beam configuration mode only horizontal motion of the source gantry (not shown) is required in order to generate a scanned image of the patient's forearm, described in greater detail below. FIG. 5B illustrates X-ray scanning of a patient's forearm 550 by using a fan beam X-ray source.

Figure 5C:
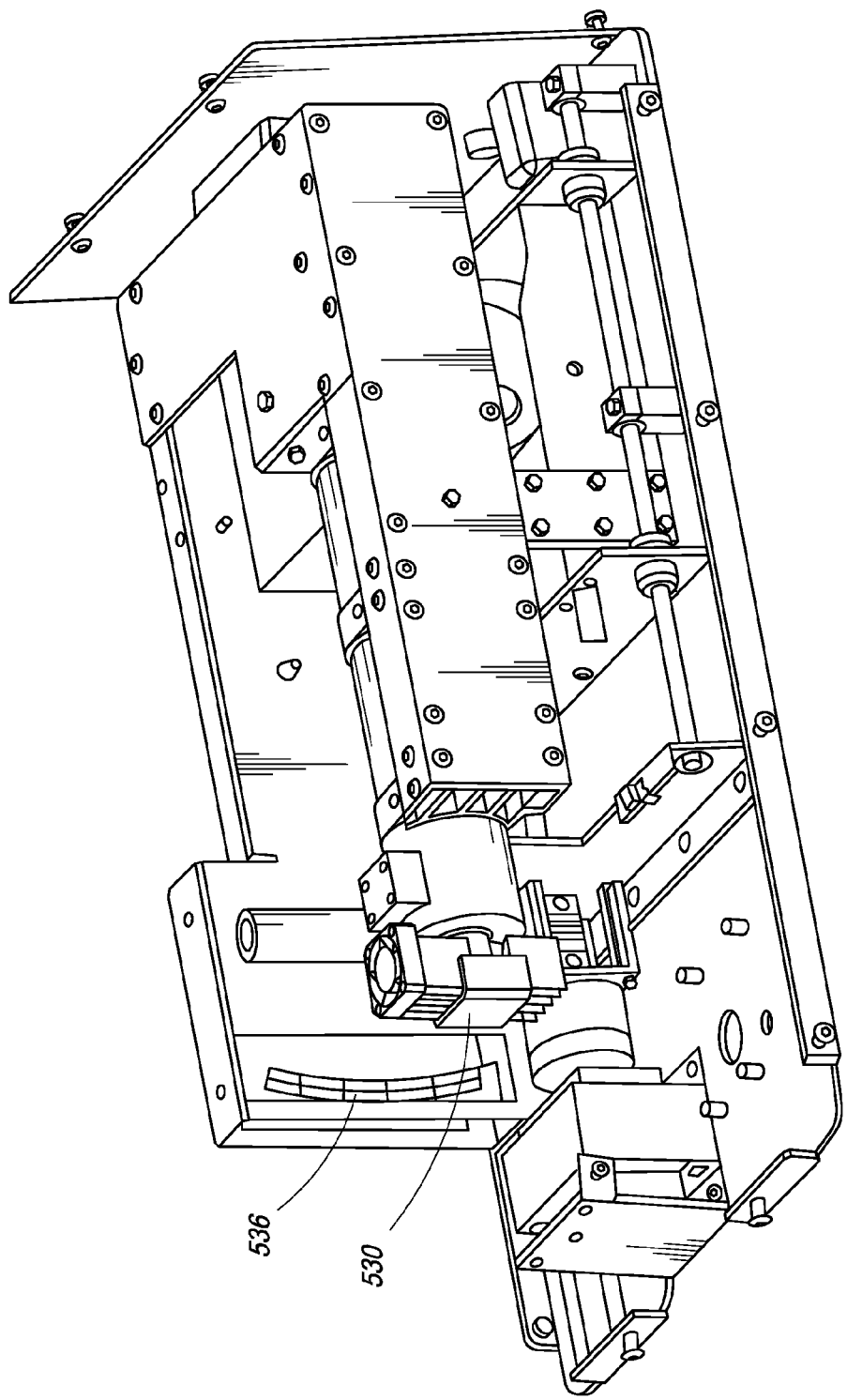
FIG. 5C illustrates a detector arrangement corresponding to a fan beam configuration mode implemented in one embodiment of the X-ray apparatus of the present invention.

FIG. 5C illustrates a detector arrangement corresponding to a fan beam configuration mode, in accordance with an embodiment of the present invention. X-ray source 530 emits a beam of X-rays, which are collimated into a fan beam, detected by arc-shaped detector array 536 which has a plurality of the aforementioned detector elements arranged in an arc shape.

FIG. 5D is an expanded view of the source and detector arrangement corresponding to a fan beam configuration mode implemented in the X-ray apparatus, in accordance with an embodiment of the present invention, showing X-ray source 530 and detector array 536. X-ray source 530 produces radiation that is collimated into a fan beam 532 which is subsequently detected by detector array 536, which comprises printed circuit boards (PCB) 535 and detector element pairs 537.

PCBs 535 are typically comprised of detector element pairs 537 placed in a row to form a small linear array. In one embodiment, each PCB comprises 16 detector elements pairs 537, where the element pairs 537 further comprise one each of a low energy detector element and a high energy detector element. In particular, in fan beam configuration mode, the PCBs 535 are arranged in the shape of an arc with the source focal point as the center. In one embodiment, the distance 538 between the X-ray source 530 and any detector element pair 537 is in the range of 140 to 200 mm, preferably 172 mm. In one embodiment, there are five PCBs 535 in the arc, thus totaling 80 element pairs 537. The five PCBs 535 are connected together from the back in a daisy-chain fashion, using a cable. Further, the PCBs 535 are mounted on a curved aluminum plate for alignment. The 5 PCB's 535 on the arc form a 5-piece linear approximation of the arc. The space between the PCB's 535 is less than half the size of one detector element, noting that if the space in-between adjacent detector elements is less than half a detector size, then it will not be noticeable in the image. In one embodiment this space is less than 1 mm. This arrangement of the detectors in the shape of an arc with the source focal point as the center is advantageous in that it allows the imaging to occur without any geometrical distortion since all the detectors placed along the arc are equidistant from the source focal point.

Figure 5E:
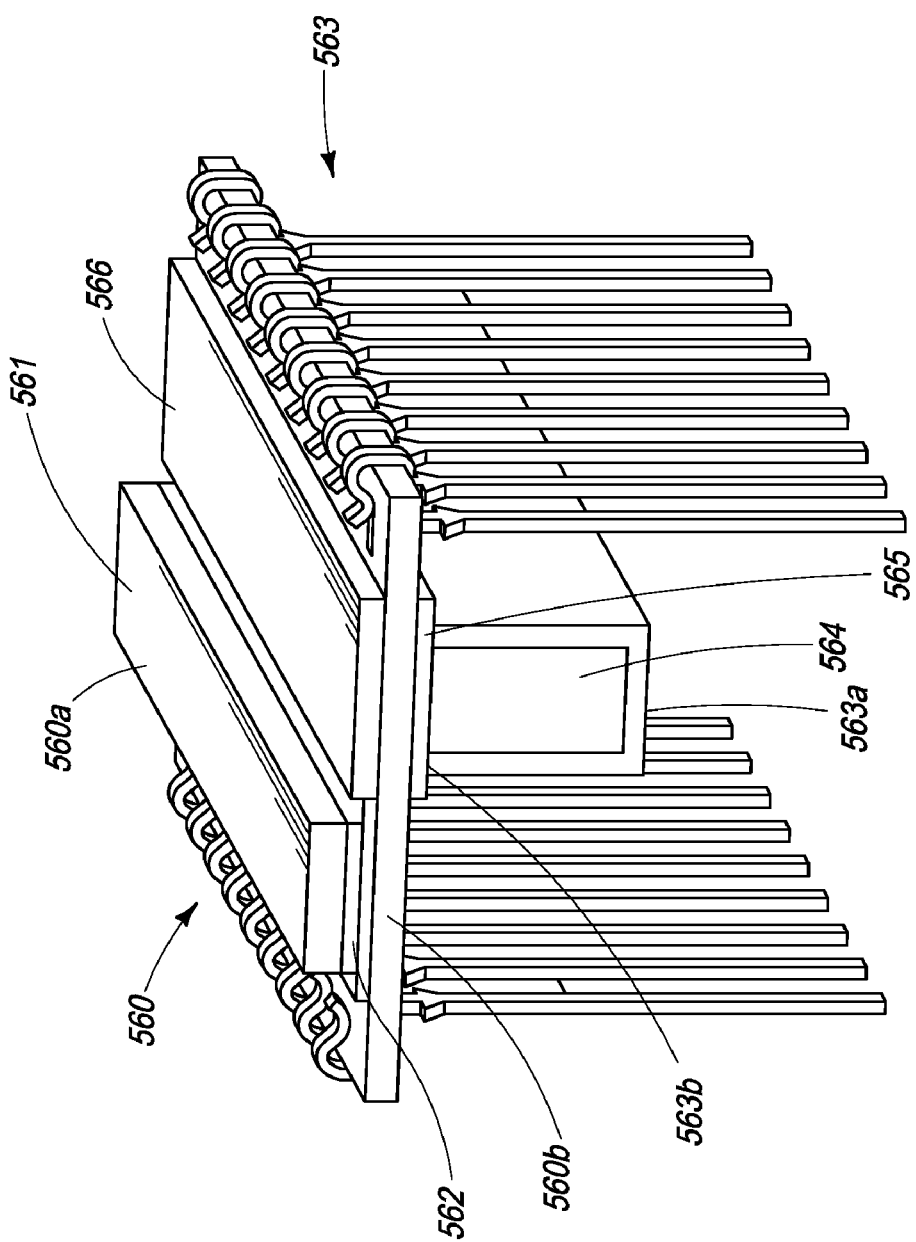
FIG. 5E illustrates a side-by-flip side detector arrangement as used in a fan beam configuration mode.

FIG. 5E illustrates a side-by-flip-side detector arrangement as used in a fan beam configuration mode. In one embodiment, the side-by-flip-side detector arrangement comprises a low energy detector element array 560, having a top side/front side 560a and a back side 560b further comprising a low energy scintillating material 561 in front side 560a and a low energy photodiode 562 in back side 560b, for detecting low energy X-ray radiation.

In one embodiment, the detector array further comprises a high energy detector element array 563, having a front side 563a and a back side 563b, further comprising high energy scintillating material 564 and a high energy photodiode 565, respectively, for detecting high energy X-ray radiation. In a side-by-flip-side configuration, low energy detector element array 560 and high energy detector element array 563 are positioned adjacent to each other, whereby the low energy component 560 is placed with its top side 560a up and whereby the high energy component 563 is placed with its back side 563b (i.e. flip side) in physical contact with the bottom of the detector holding structure. In one embodiment, a copper filter 566 is placed in the beam path of the high energy detector array 563 to attenuate most of the low energy X-ray spectrum allowing the hardened high energy X-ray spectrum to pass through, thereby enhancing the separation of the X-ray energy spectrum detected by the two detector arrays. It should be understood by those of ordinary skill in the art that the photodiode elements are placed in a small PCB having a plurality of detector element pairs, one each of high energy and low energy, in an array configuration, as described above.

Figure 5F:
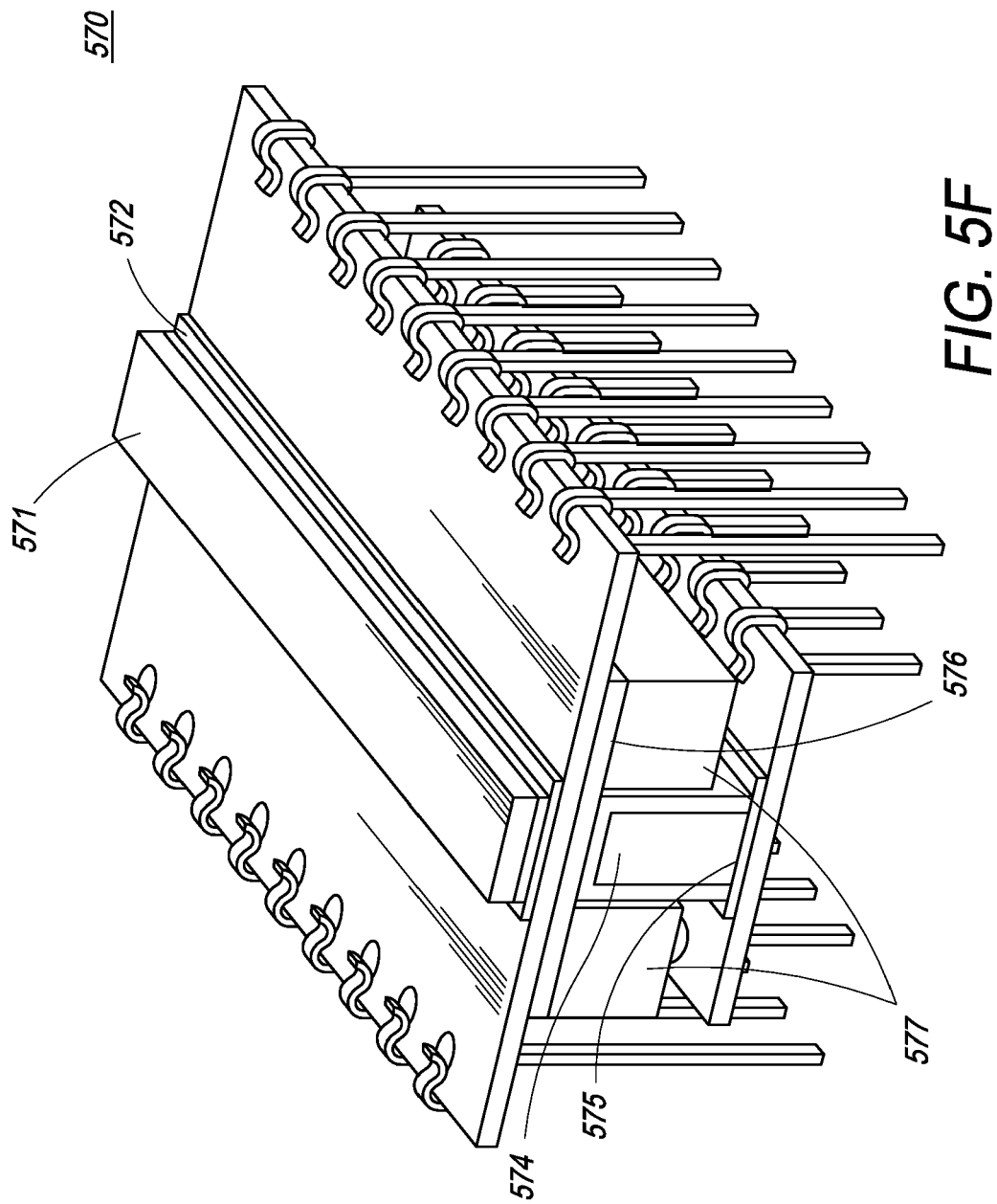
FIG. 5F illustrates a post-collimated stack detector arrangement as used in a fan beam configuration mode.

In another embodiment, the detector elements comprising a detector array are arranged in a post-collimated stack configuration. FIG. 5F illustrates a post-collimated stack detector configuration as used in a fan beam configuration mode in one embodiment of the X-ray apparatus of the present invention. As shown in FIG. 5F, the post-collimated stack detector arrangement 570 comprises a low energy scintillator material 571, placed on top of low energy photodiode 572. A copper strip 576 is placed just underneath, the low energy photodiode 572, to aid in filtering and separating the low and high energy X-rays in the energy spectrum. The post-collimated stack detector also comprises a high energy scintillator 574 and a high energy photodiode 575, positioned underneath the copper filter 576. In addition, the post-collimated stacked detector further comprises lead pieces 577 for post-collimation to eliminate scatter radiation from getting into the high energy detector.

In various embodiments of the present invention, a scanned image of the forearm is generated by concatenating single scan lines together to form a two-dimensional image. In the pencil beam configuration mode, the X-ray source is collimated to generate a narrow pencil like beam. The pair of dual energy detectors receives the pencil beam radiation and gathers pixel information. The pencil beam and detectors traverse a vertical and horizontal distance along with the gantry. During the vertical motion, individual pixels are collected to generate one scan line. During the horizontal motion, individual scan lines are gathered to form a two-dimensional image.

In the fan beam configuration mode, the X-ray source is collimated to generate a fan shaped beam that scans a vertical slice of the patient's forearm to generate one scan line. Vertical motion of the gantry is not required in the fan beam configuration mode. In an embodiment of the present invention, a linear array of dual energy detectors receive the fan beam radiation and gather scan lines as the gantry traverses the patient's forearm in a horizontal direction. Scan lines generated by the vertical slices are concatenated together to form a two-dimensional image of the forearm.

Figure 6A:
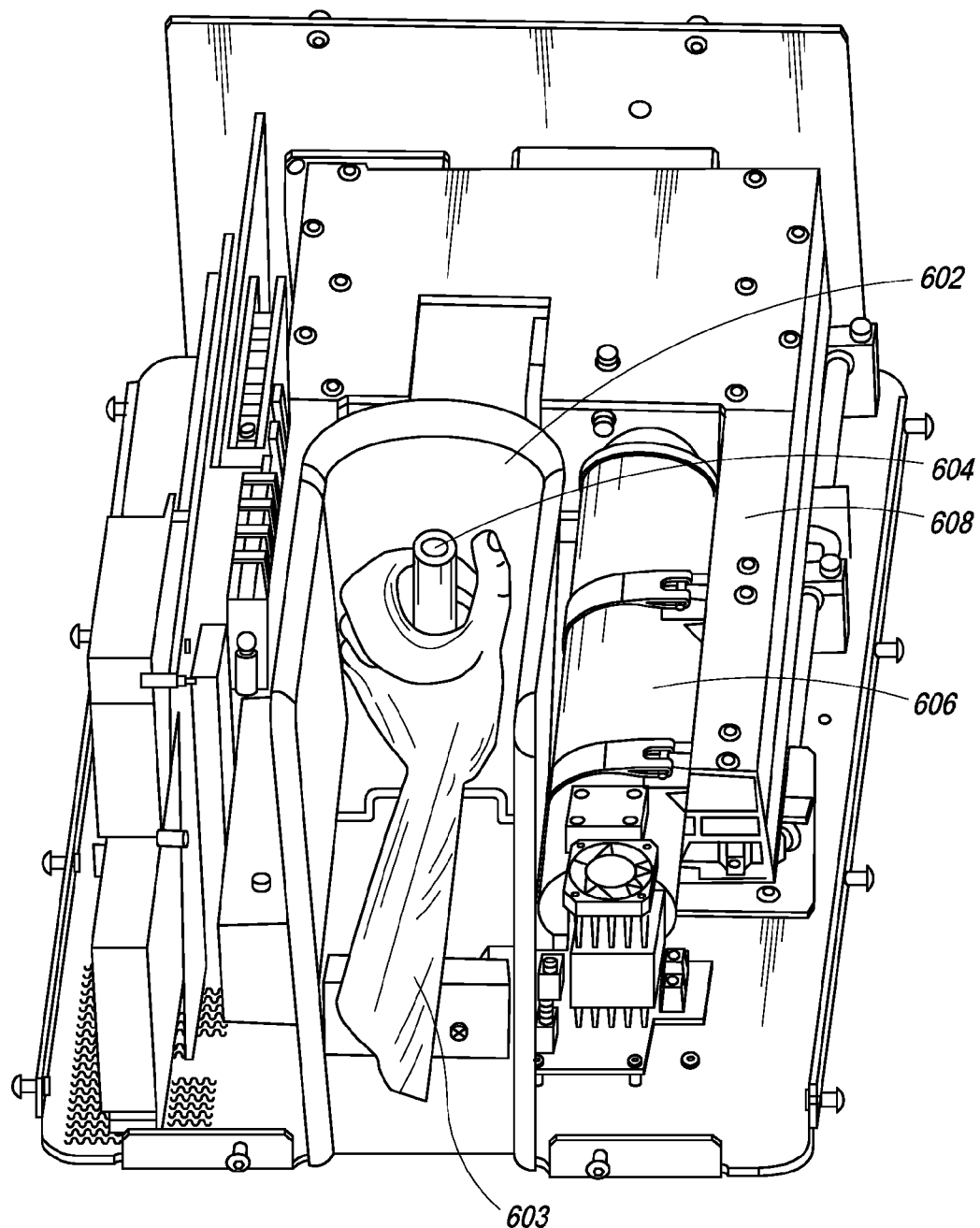
FIG. 6A illustrates a patient's forearm placed in an arm rest of the dual energy X-ray apparatus, further showing a fist grasping a holding bar.

FIG. 6A illustrates a patient's forearm 603 placed in the arm rest 602 of the dual energy X-ray apparatus with a fist around the holding bar 604. The patient is required to keep the forearm 614 in the position illustrated in FIG. 6A. Gantry 608 is movable, as described below with respect to FIGS. 6B and 6C, and thus enables quick and efficient scanning without requiring the patient to re-position the forearm. Radiation source 606 is located on the gantry 608, and moves with the gantry 608, as does the detector array (not shown). In various embodiments of the present invention, the dual energy X-ray system 600 is connected to a computer comprising memory for storing a database for archiving the scanned wrist image, calculating bone mineral density, maintaining a history of patient information, generating patient history reports, and presenting several graphical user interfaces (GUIs) that enable both the operation and use of the scanning system. The result is a consistent scan of the wrist area during every scanning session. Also, the patient is not required to reposition the forearm 614 at any time during the scan.

Figure 6B:
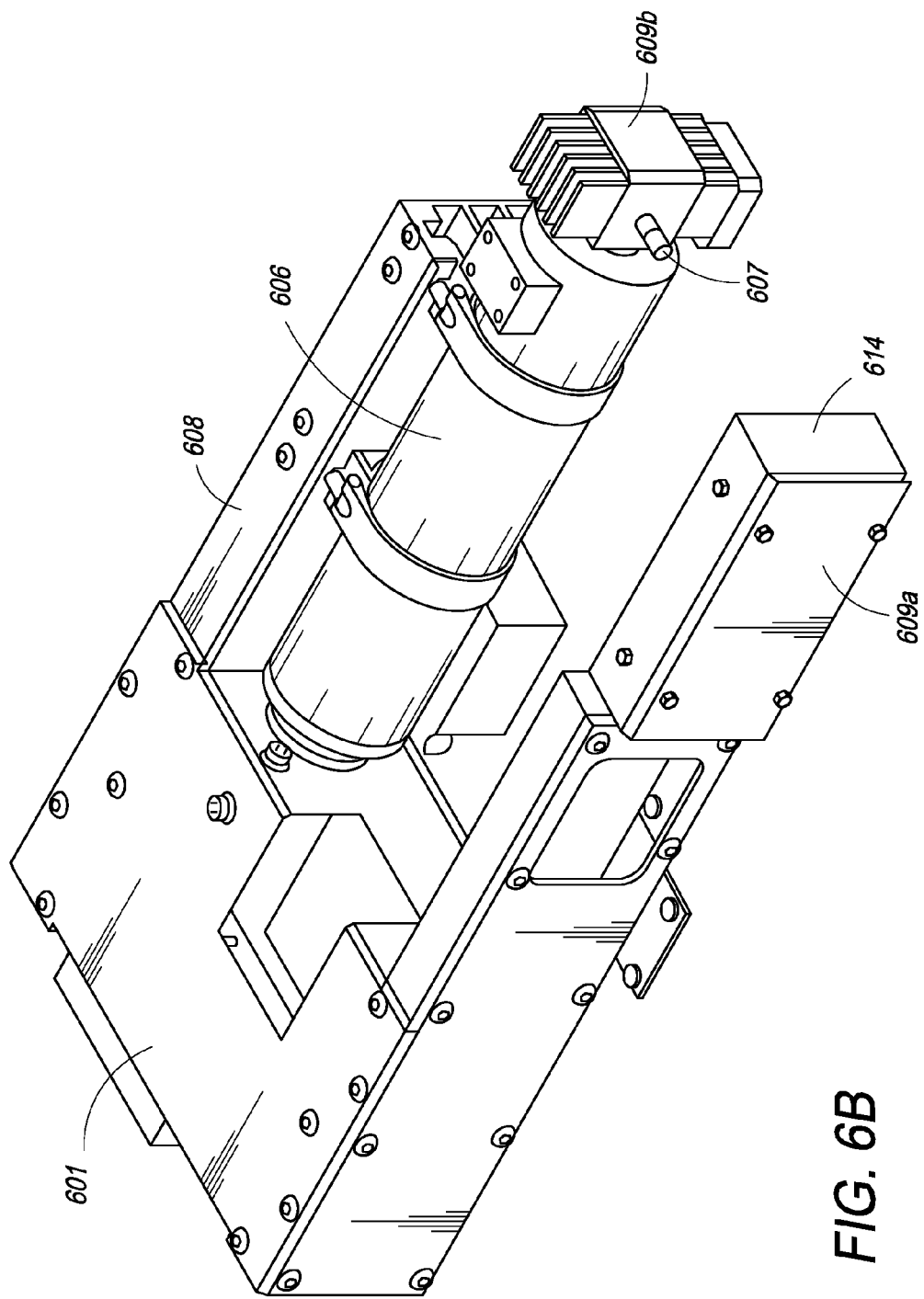
FIG. 6B is a view of a gantry coupled with an X-ray tube, in accordance with an embodiment of the present invention.

FIG. 6B is a view of the X-ray tube 606, coupled to gantry 608, in accordance with an embodiment of the present invention. In addition, detector array 614 is also coupled to gantry 608 and positioned across from X-ray source aperture 607. As mentioned above, depending on whether the radiation beam is a pencil beam or fan beam, the detector array may comprise one detector element pair or a plurality of element pairs. In various embodiments of the present invention, the gantry 608 is capable of moving in both an angular/rotational direction and a horizontal direction. In general, the gantry is a U-shaped gantry wherein the base 601 is hinged and the two distal end prongs of the gantry 609a and 609b move in a horizontal and/or angular motion around a stationary arm.

Figure 6C:
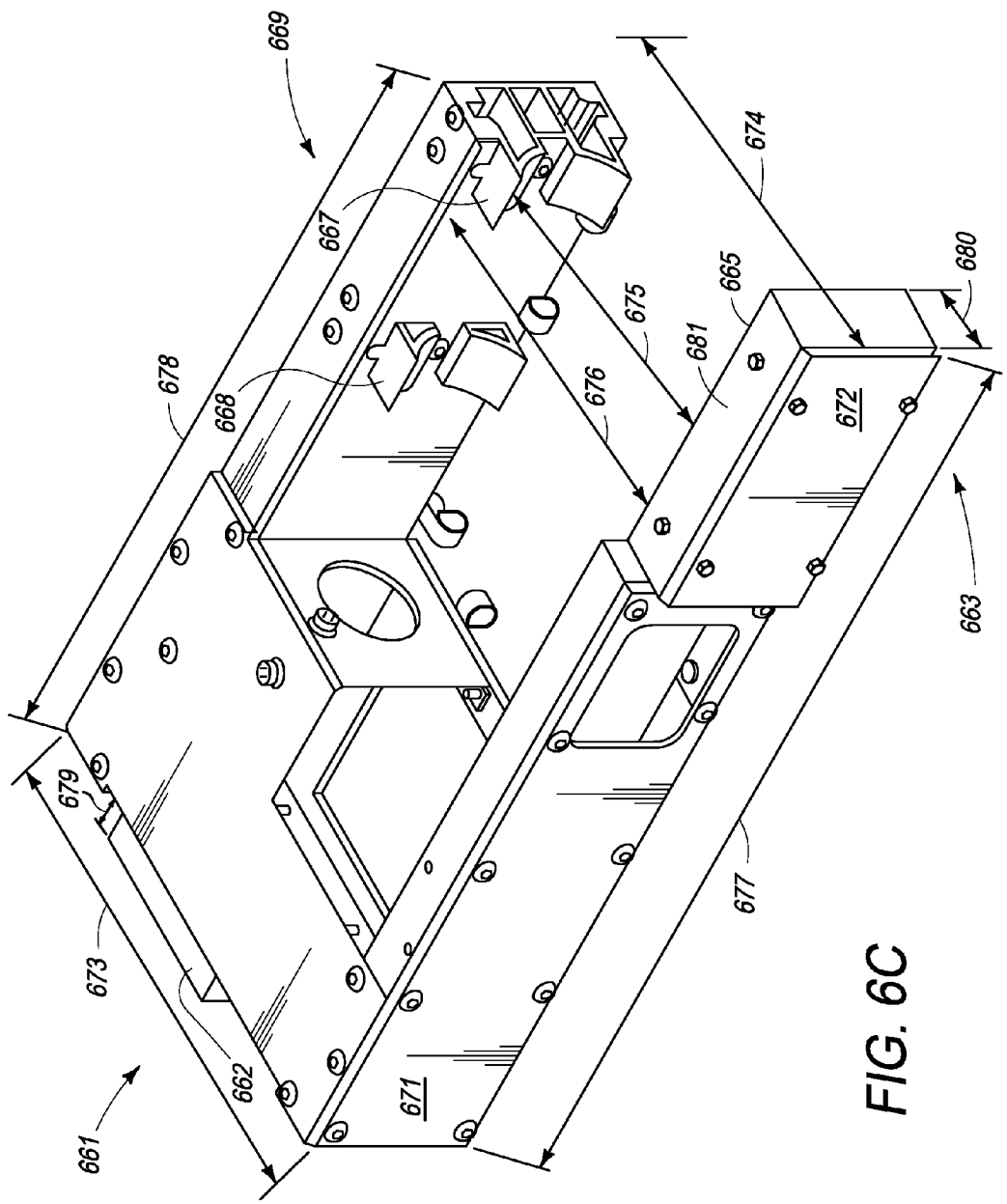
FIG. 6C is a detailed break-away view of the gantry of the present invention, showing overall dimensions of the gantry.

FIG. 6C is a detailed break-away view of the gantry of the present invention, showing overall dimensions of the gantry 608. Gantry 608 has a proximal end 661, which is attached to the system housing (not shown) using mounting bracket 662, and a distal end 663. The overall height 671 of the system proximate to the proximal end 661 is in the range of 70.5 mm and 105.5 mm, and is preferably approximately 88 mm. The overall height 672 of the system proximate to the distal end 663 is in the range of 57.6 mm and 86.4 mm, and is preferably approximately 72 mm. The overall width 673 of the system at the proximal end 661 is in the range of 208.4 mm and 312.6 mm, and is preferably approximately 260.5 mm. The overall width 674 of the system at the distal end 663 is in the range of 217.6 mm and 326.4 mm, and is preferably approximately 272 mm. The width 675 between the inner surface 665 of the distal end 663 and an outer source mounting bracket 667 is in the range of 134 mm and 201 mm, and is preferably approximately 167.4 mm. The width 676 between inner surface 665 and inner surface 668 is in the range of 150.8 mm and 226.2 mm, and is preferably approximately 188.5 mm. The width 680 of the detector box 681 is in the range of 34.88 mm and 52.32 mm and, is preferably approximately 43.6 mm. The length 677 from proximal end 661 to distal end 663 is in the range of 400.1 mm and 600.1 mm, and is preferably approximately 500.1 mm on the side opposite the X-ray source mounting side 669. The length 678 from proximal end 661 to distal end 663 on the side 669 upon which the X-ray source (not shown) is mounted is in the range of 320.8 mm and 481.2 mm, and is preferably approximately 401 mm. The length 679 of the counter-weight bracket 662 is in the range of 12.7 mm and 19.1 mm and, is preferably approximately 15.9 mm.

Figure 6D:
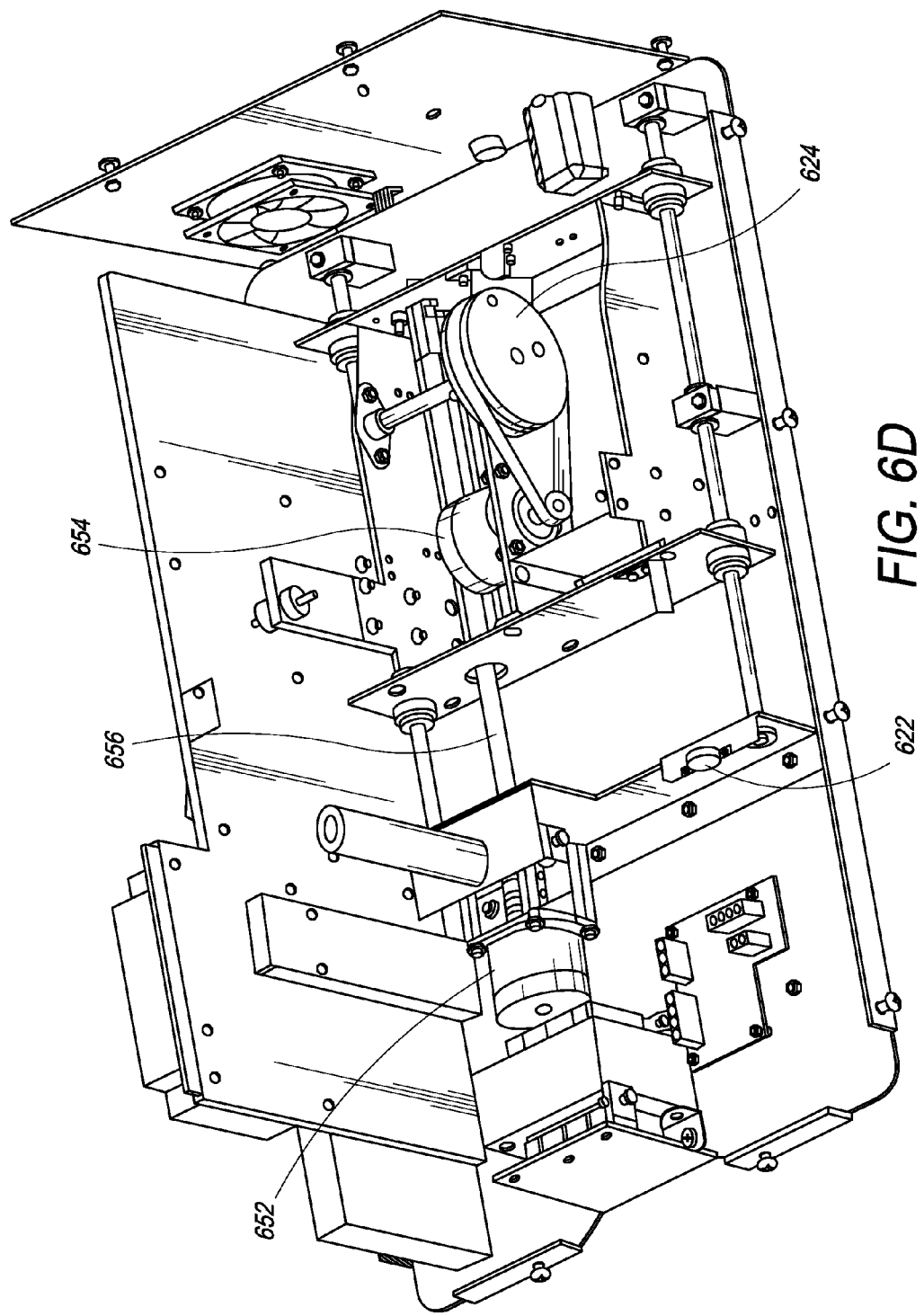
FIG. 6D illustrates a motor assembly that facilitates horizontal motion of the gantry and at least one optical sensor for detecting the position of the gantry during motion, in accordance with an embodiment of the present invention.

The movement of the gantry 608 is managed by a motor assembly, as shown in FIG. 6D, upon which the gantry 608 is mounted. When a scan of a patient's forearm is initiated, the gantry moves to at least one position. In one embodiment, a gantry position is detected using at least one optical sensor that is triggered when the gantry 608 reaches its position. FIG. 6D also illustrates the optical sensors, in accordance with an embodiment of the present invention. In one embodiment, a first optical sensor 622 is triggered by a metal plate when the gantry is in a first, horizontal position. In another embodiment, a second optical sensor 624 is triggered every time a full angular motion is completed. In one embodiment, a first position is reached when both optical sensors are triggered. FIG. 6D also illustrates a motor assembly that facilitates horizontal motion and angular motion of the gantry, in accordance with an embodiment of the present invention. Motor assembly components 652 and 654 enable movement of a gantry carrying an X-ray tube in a horizontal direction and a vertical direction respectively. The gantry is mounted on top of the motor assembly 652 and 654. A lead screw 656 aids horizontal motion.

Figure 6E:
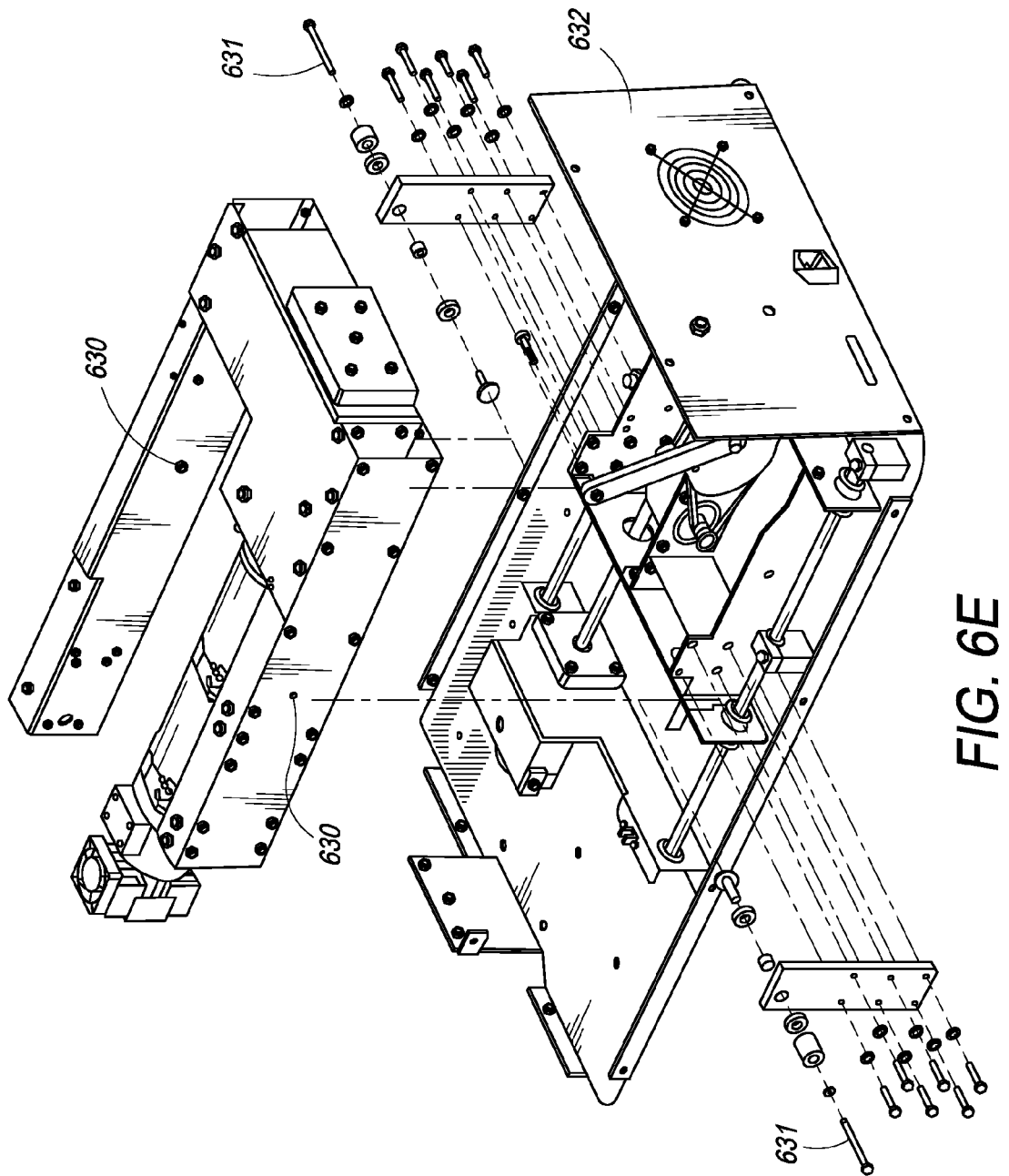
FIG. 6E is a detailed break-away view of the gantry of the present invention, showing pivot points of the gantry.

FIG. 6E is a detailed, break-way view of the gantry portion of the present invention, showing pivot points of the gantry. As mentioned above, gantry 608 is capable of movement in a vertical or angular motion (wherein the angular motion is equivalent to a vertical translation) and horizontal displacement. Gantry 608 comprises pivot points 630 for angular motion of the gantry. Also referring to FIG. 6E, pivot points 630 are removably attached, using mounting hardware 631, to the housing 632 of the system of the present invention.

Figure 7A:
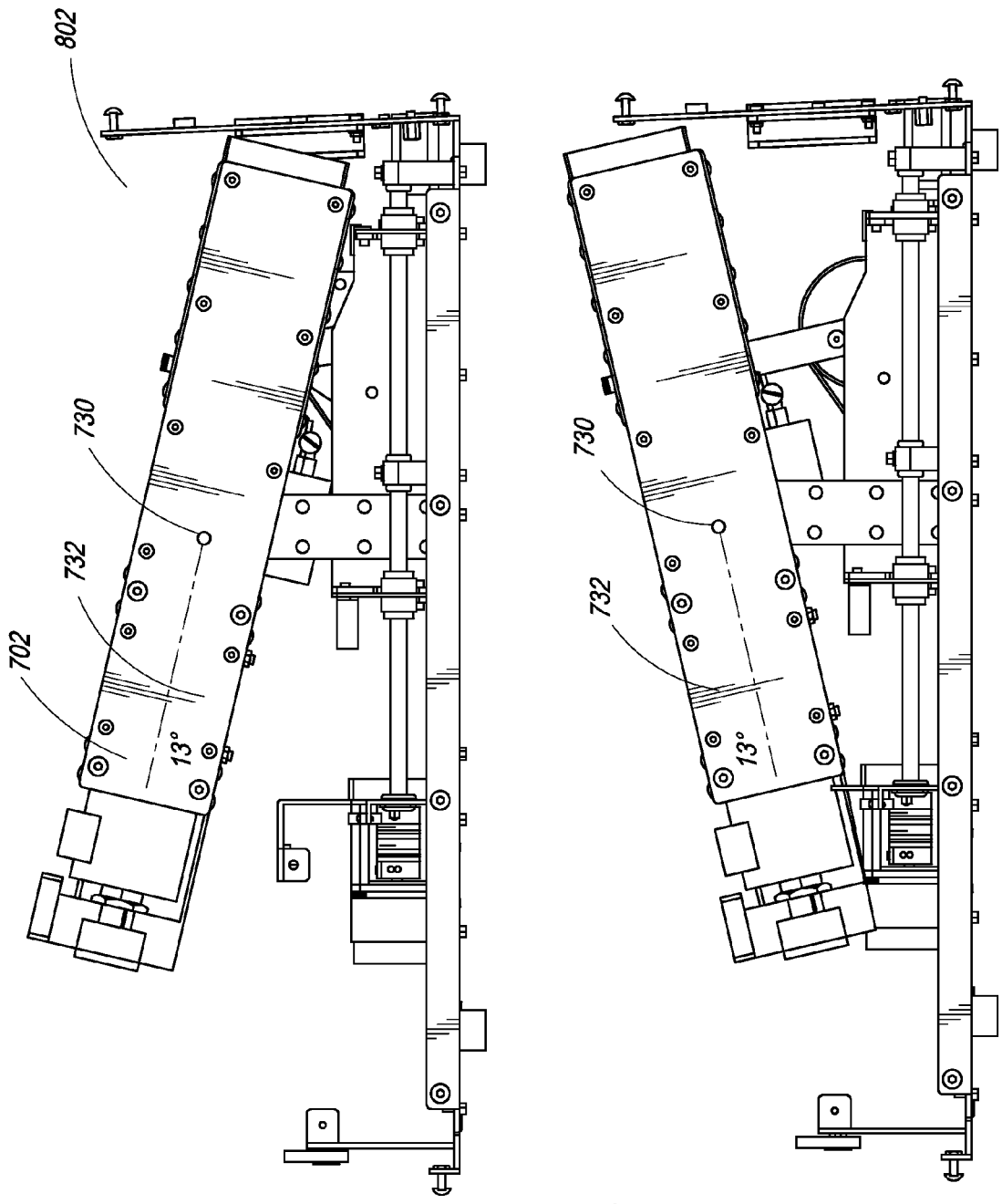
FIG. 7A illustrates the overall range of angular motion of the gantry.
Figure 7B:
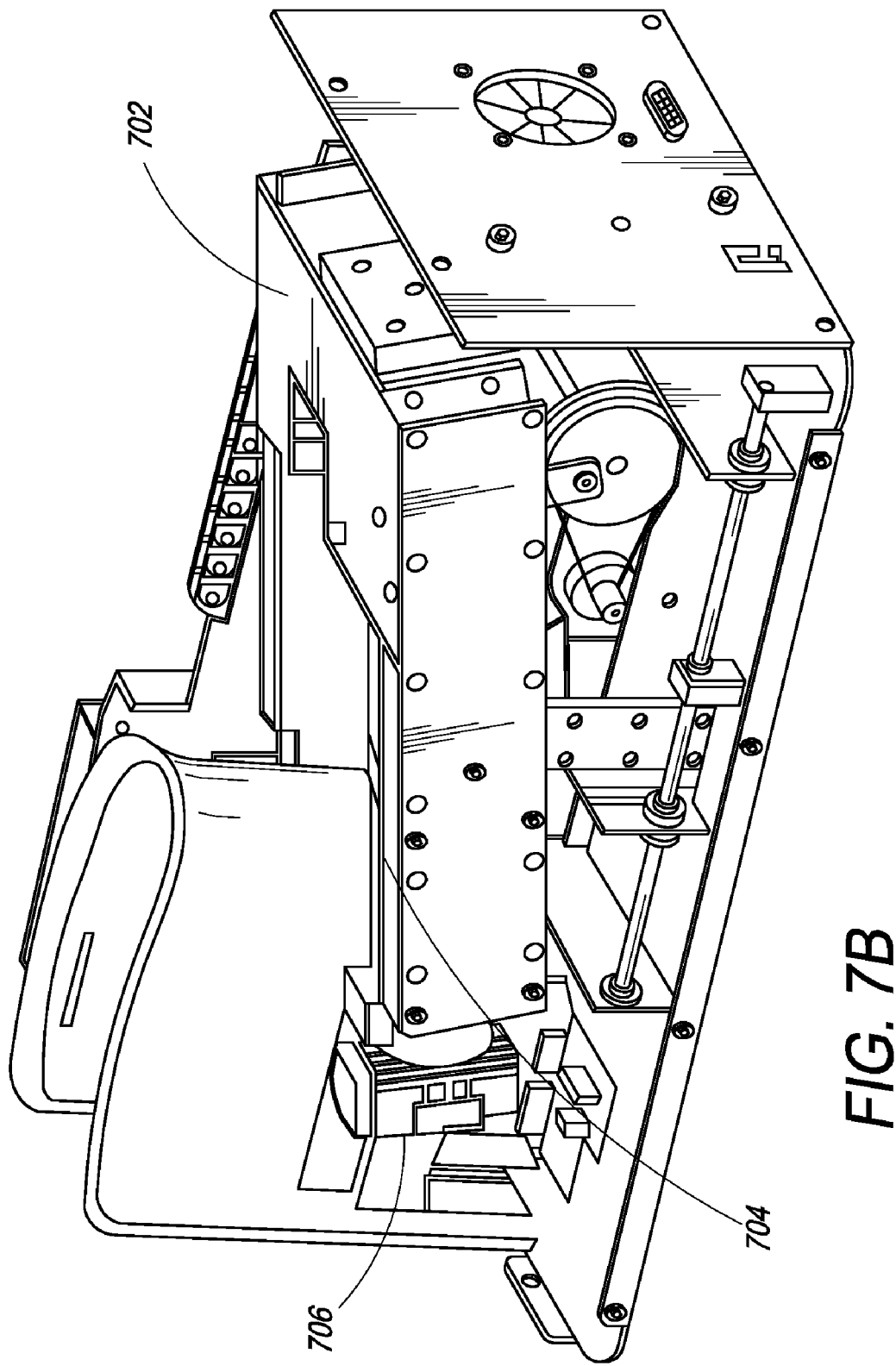
FIG. 7B illustrates a first position of the gantry during angular motion, in accordance with an embodiment of the present invention.
Figure 7C:
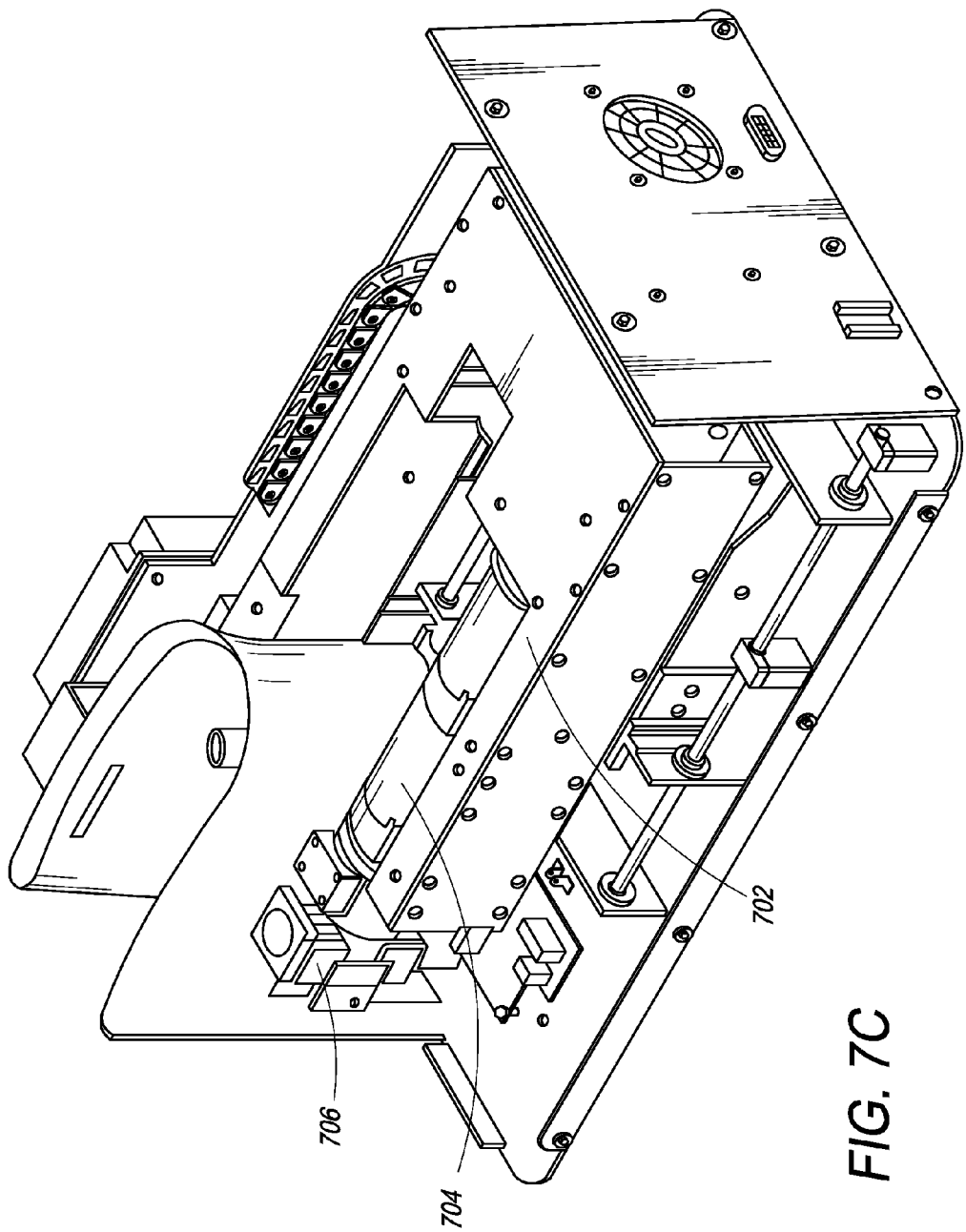
FIG. 7C illustrates a second position of the gantry during angular motion, in accordance with an embodiment of the present invention.
Figure 7D:
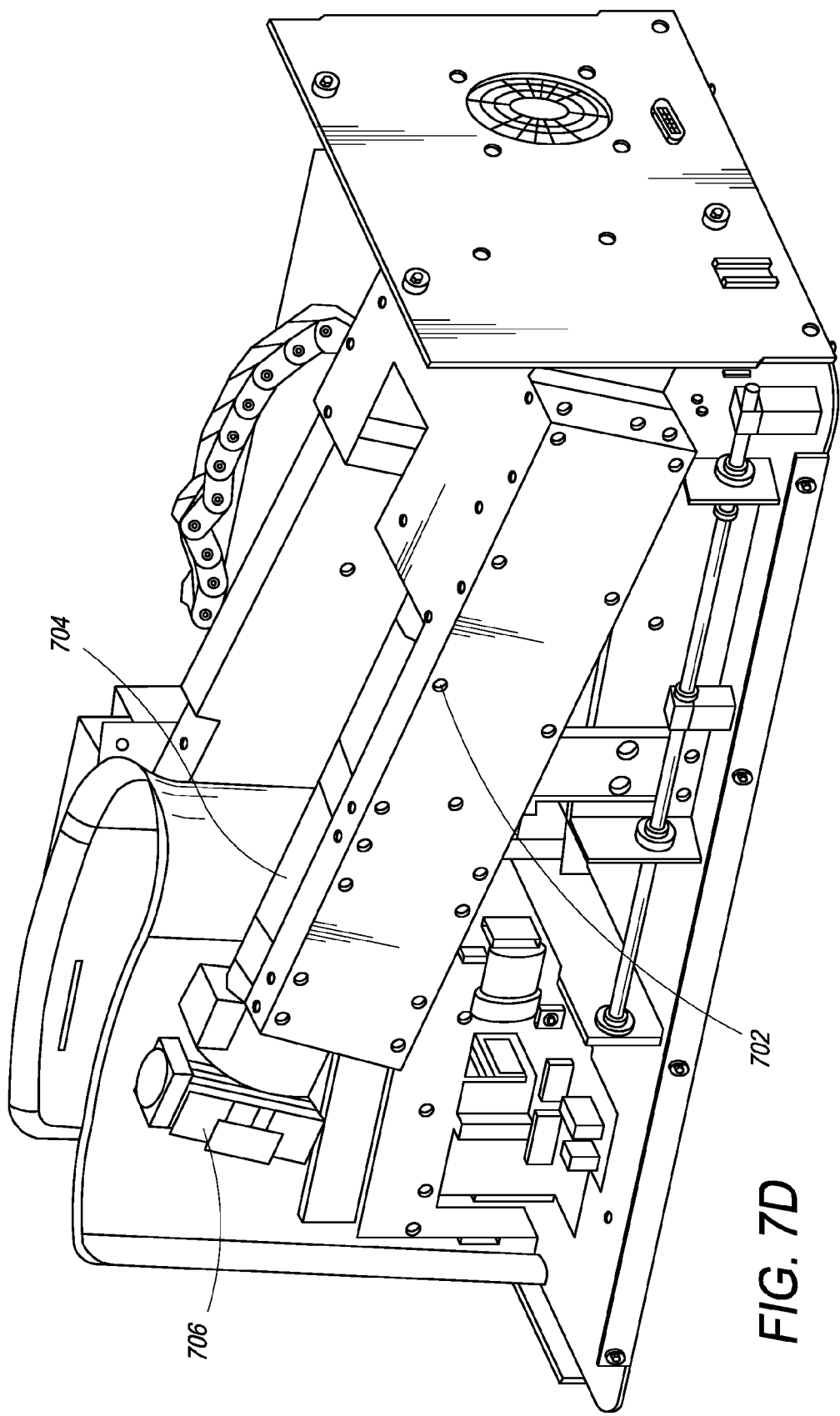
FIG. 7D illustrates a third position of the gantry during angular motion, in accordance with an embodiment of the present invention.

FIGS. 7A, 7B, 7C, and 7D illustrate angular motion of the gantry, in accordance with an embodiment of the present invention. As shown in FIGS. 7A, 7B, 7C and 7D, gantry 702 is coupled with X-ray tube 704. Referring to FIGS. 7B, 7C, and 7D, X-ray tube 704 comprises an X-ray source 706 and at least a pair of dual energy detectors (not shown).

Now referring to FIG. 7A, gantry 702 is capable of moving about pivot points 730 in the range of +20 degrees to −20 degrees, from a 0 degree position. Now referring to FIG. 7A, gantry 702 is, in one preferred embodiment, capable of moving about pivot points 730 a total of +13 degrees from a 0 degree position 732, which is equivalent to a total vertical displacement of 111 mm. Gantry 702 can also move about pivot points 730 a total of −13 degrees from a 0 degree position 732, which is equivalent to a total vertical displacement of 99 mm.

FIG. 7B illustrates a first position of the gantry 702 wherein the X-ray source 706 is at a bottom most position, approximately −13 degrees from a zero degree position, and enables scanning of the bottom portion of the patient's forearm (not shown). FIG. 7C illustrates a second position of the gantry 702 wherein the X-ray source 706 is at a center or zero degree position and enables scanning of a mid-portion of the patient's forearm (not shown). FIG. 7D illustrates a third position of the gantry 702 wherein the X-ray source 706 is at a top-most position, or approximately +13 degrees from a zero degree position, and enables scanning of an upper portion of the patient's forearm (not shown). The total vertical linear distance traversed by the angular motion is in the range of 210 mm (from −13 degrees to +13 degrees) and 296 mm (from −20 degrees to +20 degrees), and is preferably 210 mm.

Figure 8A:
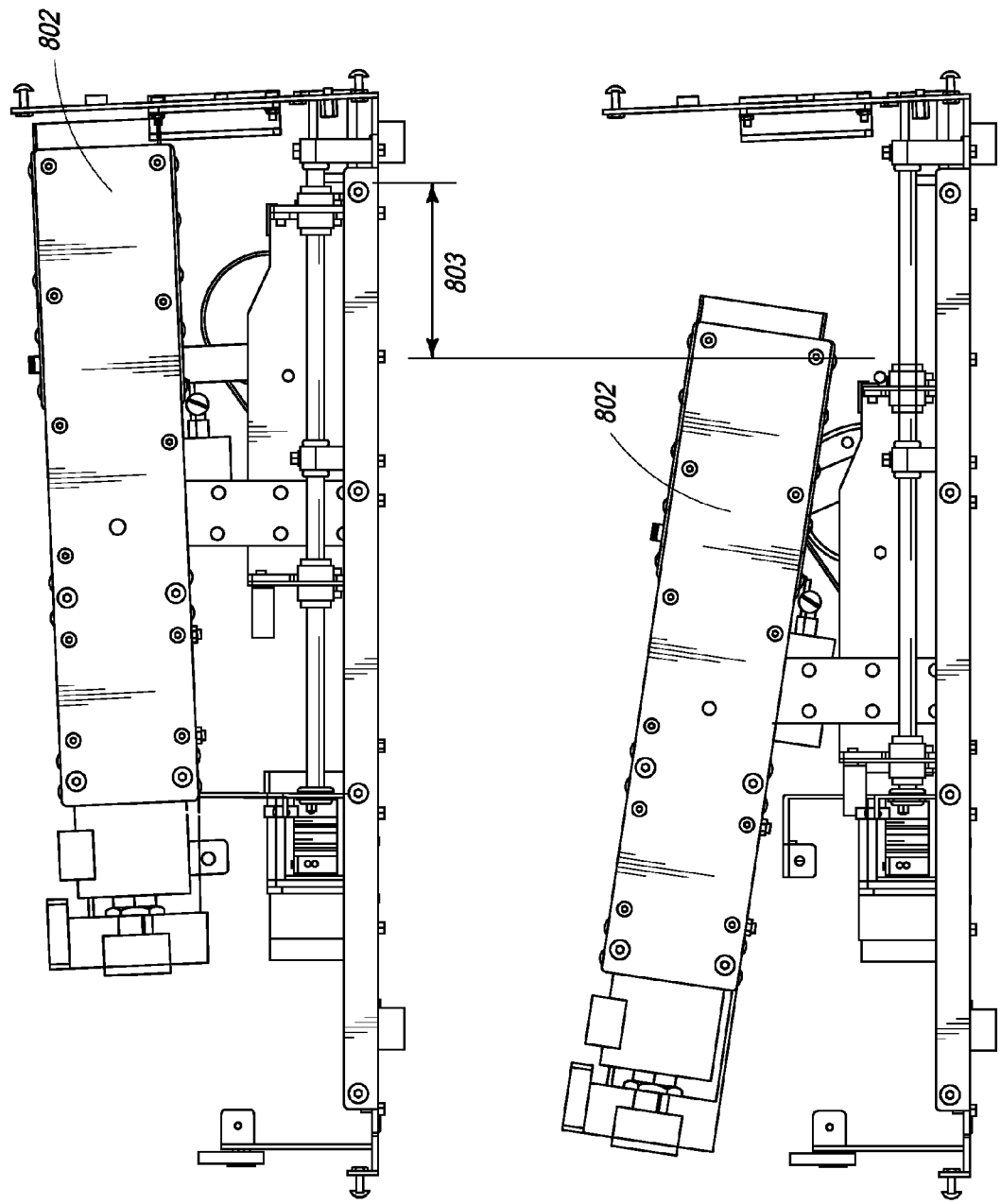
FIG. 8A illustrates the overall range of horizontal motion (displacement) of the gantry.
Figure 8B:
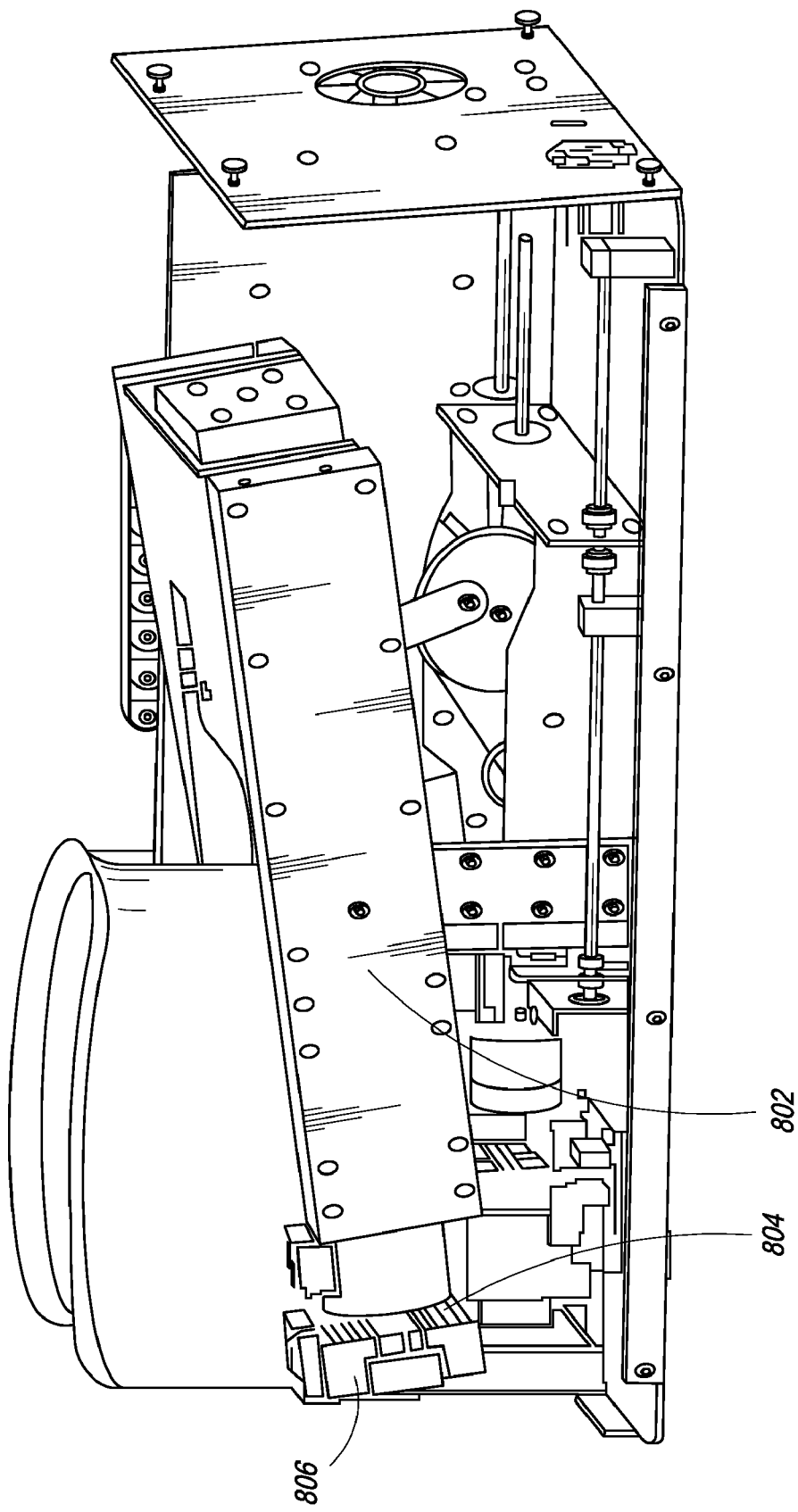
FIG. 8B illustrates a first position of the gantry during horizontal motion, in accordance with an embodiment of the present invention.
Figure 8C:
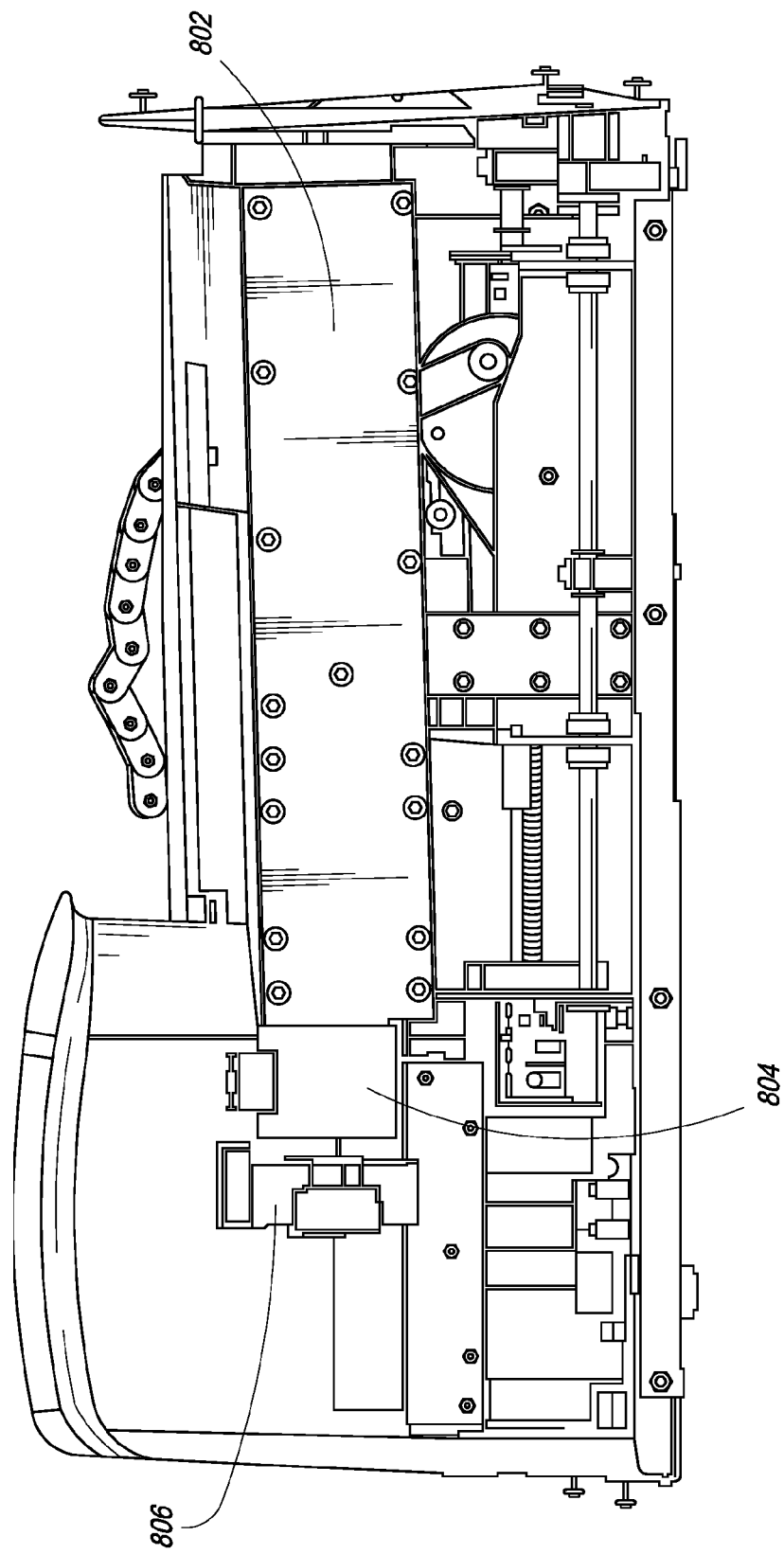
FIG. 8C illustrates a second position of the gantry during horizontal motion, in accordance with an embodiment of the present invention.

FIGS. 8A, 8B, and 8C illustrate a horizontal motion of the gantry, in accordance with an embodiment of the present invention. FIG. 8A illustrates the overall horizontal displacement 803 of the gantry 802. In one embodiment, the total horizontal displacement is 105 mm.

FIGS. 8B and 8C illustrate a gantry 802 coupled with X-ray tube 804. The X-ray tube 804 comprises an X-ray source 806 and at least a pair of dual energy detectors (not shown). FIG. 8B8A illustrates a first position of the gantry 802 wherein the X-ray source 806 is at a forward most position and enables scanning of a rear portion of the patient's forearm (not shown) furthest away from the wrist. FIG. 8C8B illustrates a second position of the gantry 802 wherein the X-ray source 806 is at a back most position and enables scanning of a forward portion of the patient's forearm closest to the wrist.

Figure 9:
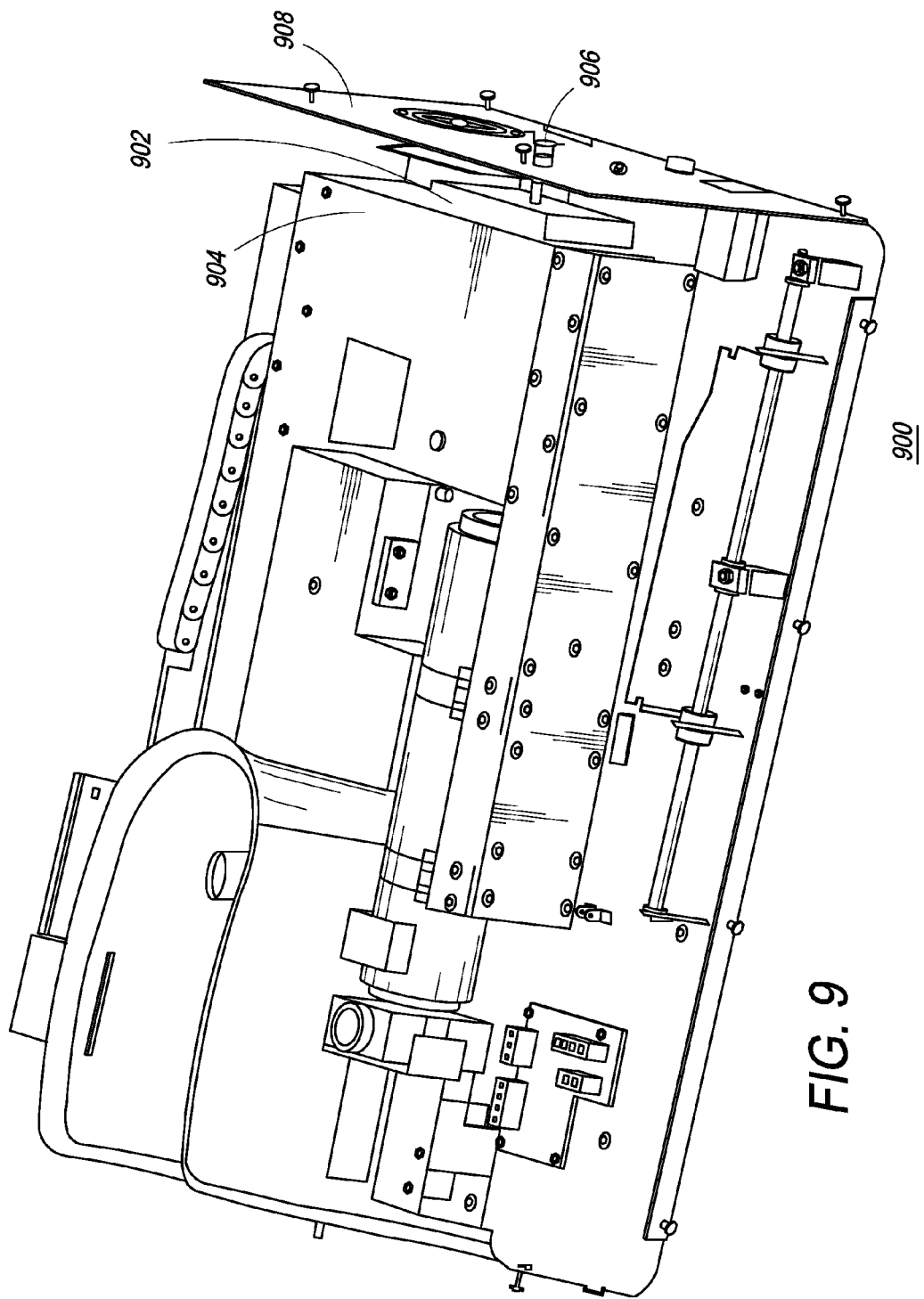
FIG. 9 illustrates a locking mechanism for transportation of the dual energy X-ray apparatus, in accordance with an embodiment of the present invention.

FIG. 9 illustrates a locking mechanism for secure and easy transportation of the dual energy X-ray apparatus 900, in accordance with an embodiment of the present invention. A counter weight 902 is attached to a gantry 904. A bolt 906 is placed through a back plate 908 into the counter weight 902. The bolt secures the gantry 904 in place for transportation of the dual energy X-ray apparatus 900, thus inhibiting any movement of the gantry 904.

Figure 10:
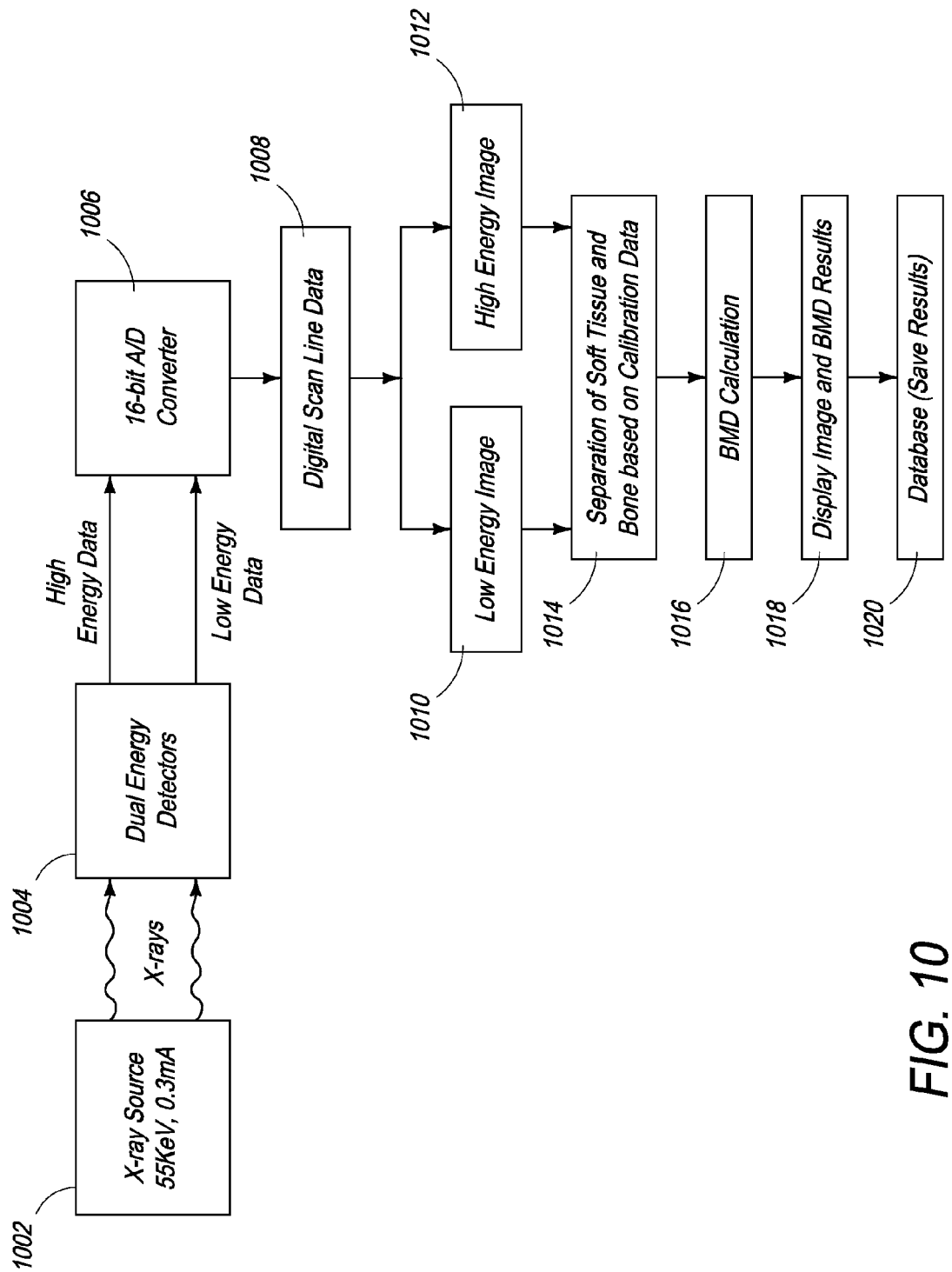
FIG. 10 illustrates overall data flow in the dual energy X-ray apparatus, in accordance with an embodiment of the present invention.

FIG. 10 illustrates overall data flow in the dual energy X-ray apparatus, in accordance with an embodiment of the present invention. X-rays produced by an X-ray source at step 1002 pass through a patient's forearm and are detected by dual energy detectors at step 1004, which in turn, produce high energy and low energy data. The data produced is processed by a 16 bit analog to digital converter at step 1006 to produce digital scan line data at step 1008. The digital scan line data is used to produce a low energy image and a high energy image at steps 1010 and 1012, respectively. The produced low and high energy images are processed along with the calibration data to separate soft tissue from bone at step 1014. Bone mass density calculations are performed at step 1016 by using the separated bone data. At step 1018 the produced images and the calculated BMD are displayed. At step 1020 the displayed data is also stored in a database.

Figure 11A:
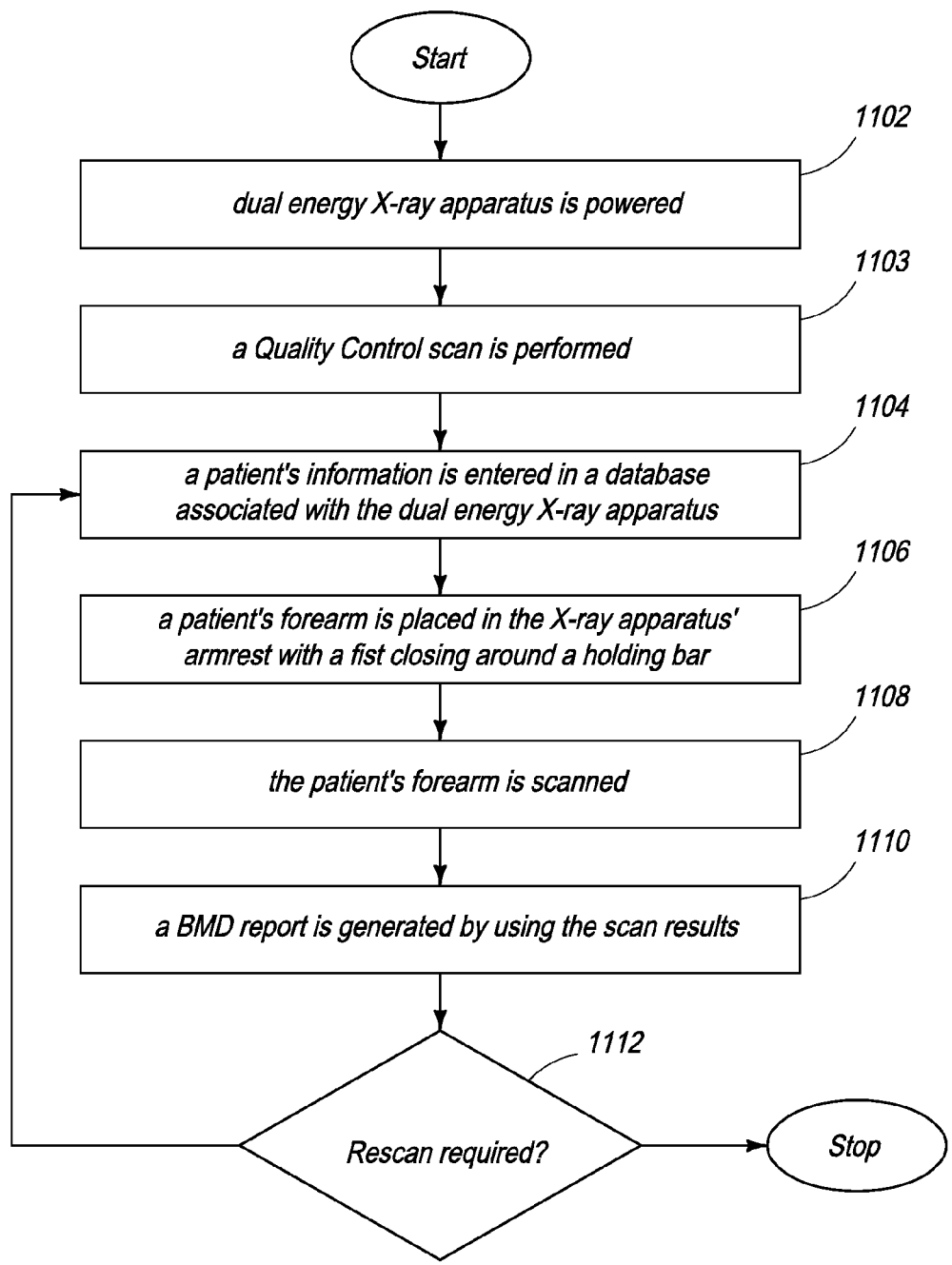
FIG. 11A is a flowchart illustrating a method for measuring bone mass density by using the dual energy X-ray apparatus, in accordance with an embodiment of the present invention.

FIG. 11A is a flowchart illustrating a method for measuring bone mass density using the dual energy X-ray apparatus of the present invention. In one embodiment, at step 1102, the dual energy X-ray apparatus is powered on and operated using a GUI located on a display of a monitor operably connected to a computing system that is operably connected to the X-ray scanning apparatus of the present invention. In one embodiment, the power supply in the apparatus is a universal power input ranging from 90 VAC to 260 VAC using a switching power supply. Thus, the unit is usable in all countries, without the need for voltage conversion modules installed on the input AC power line.

Figure 11B:
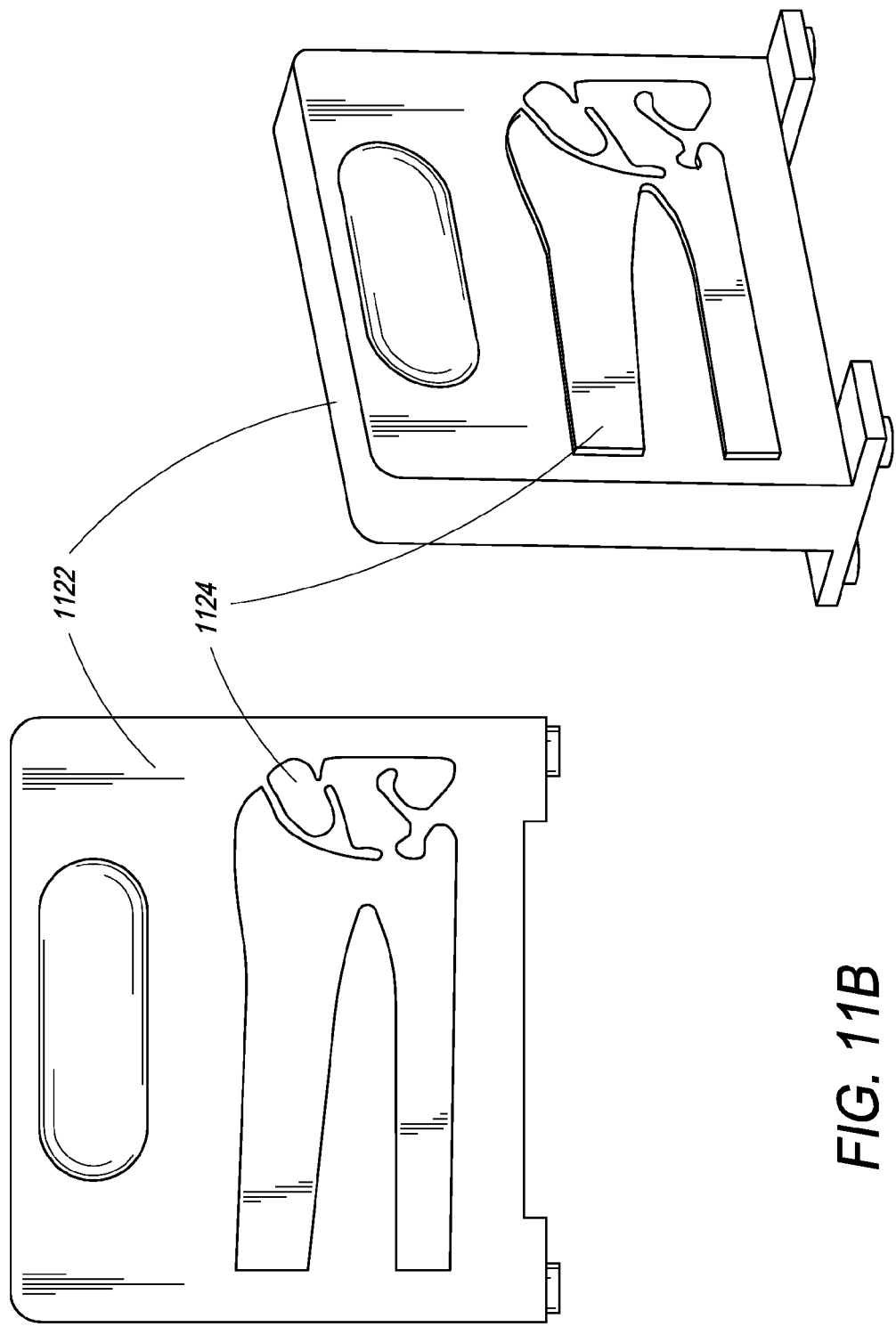
FIG. 11B shows two perspective illustrations of a forearm phantom used for performing the power up calibration, in accordance with an embodiment of the present invention.

In an embodiment of the present invention, a Quality Control scan is run on the X-ray apparatus at step 1103 right after powering the apparatus in order to ensure that the apparatus is in calibration. Calibration must be performed after each power cycle of the apparatus to ensure that the detector array response to radiation is within operating limits. Calibration is performed by running a Quality Control Scan using a phantom of a patient's forearm. FIG. 11B illustrates a forearm phantom 1124 used for performing the power up calibration, in accordance with an embodiment of the present invention. Detector response to radiation passing through phantom forearm 1124 contained in a plastic housing 1122 is gathered and verified based on a calibration table that is stored in the dual energy X-ray apparatus. The calibration table for each apparatus is generated in the factory based on several hundred calibration scans where data is gathered from the apparatus at full X-ray beam attenuation, no X-ray beam attenuation, and partial X-ray beam attenuation through varying material thickness.

Referring back to FIG. 11A, at step 1104 a patient's information is entered in a database associated with the dual energy X-ray apparatus. In one embodiment, patient information corresponding to all patients scheduled for the day is pre-entered at the beginning of the day in order to minimize the patient observation time. Thus, patient information can be pre-loaded into the database to minimize scan time.

Figures 11C, 11D:
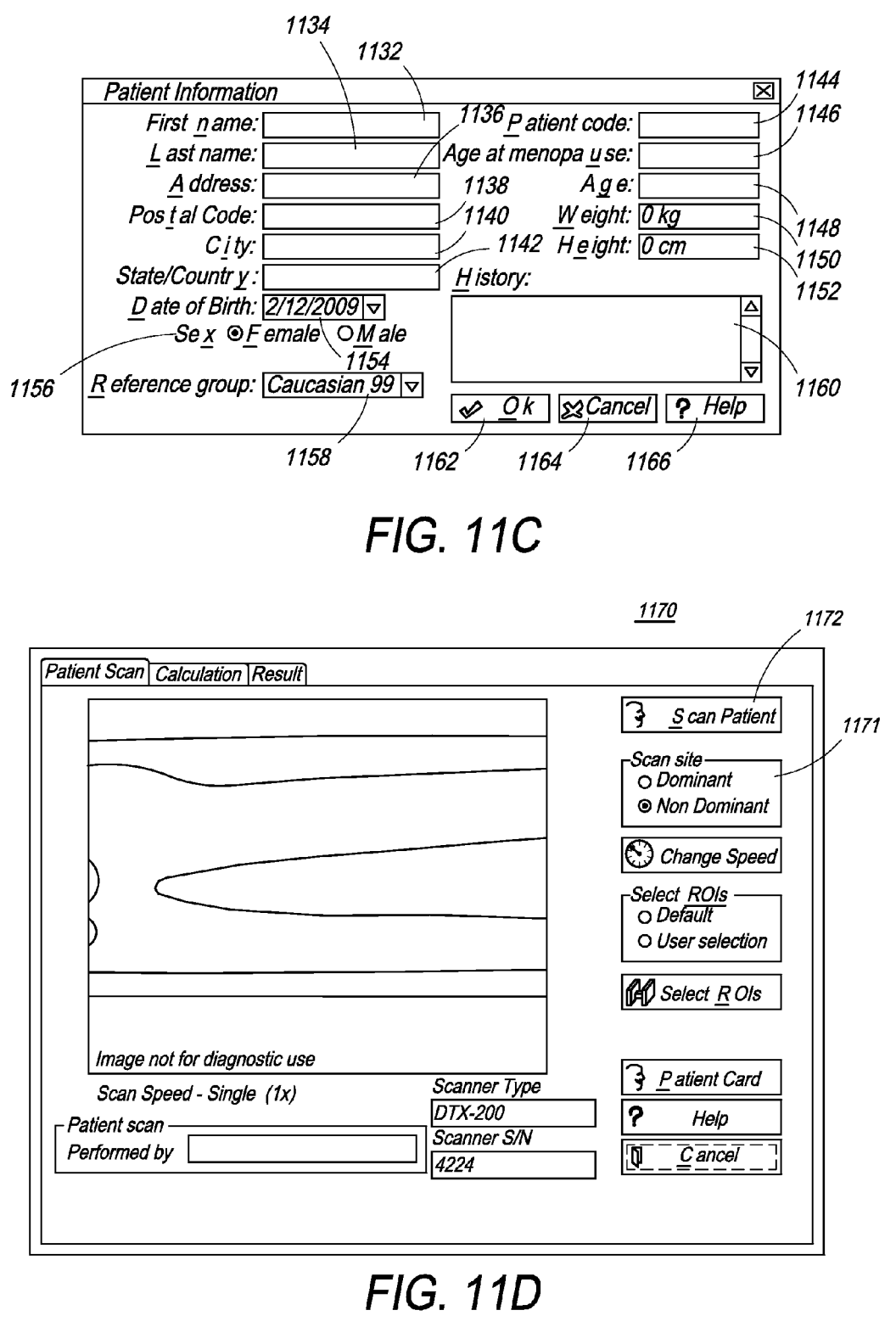

FIG. 11C is a screenshot of an exemplary GUI electronic form that may be used to enter patient information or parameters in a database, in accordance with an embodiment of the present invention. The electronic form comprises a textbox 1132 for entering a patient's first name, a textbox 1134 for entering a patient's last name, a textbox 1136 for entering a patient's street address, a textbox 1138 for entering a patient's postal code, a textbox 1140 for entering a patient's city of residence, a textbox 1142 for entering a patient's state/country of residence, a textbox 1144 for entering a unique patient identification code, a textbox 1146 for entering a patient's age at menopause, (textbox 1148 will automatically be filled based on date of birth information entered in box 1154), a textbox 1150 for entering a patient's weight, a textbox 1152 for entering a patient's height, a drop down select box 1154 for entering a patient's date of birth, a select box 1156 for entering a patient's gender, a drop down select box 1158 for entering a patient's reference group, a text box 1160 for entering a patient's medical history, a button 1162 labeled 'OK' for storing the entered information in the database, a button 1164 labeled 'Cancel' for erasing the entered information and a button 1166 labeled 'Help' for accessing support documentation.

Referring back to FIG. 11A, at step 1106 the patient's forearm is placed in the X-ray apparatus' armrest with a fist closing around a holding bar, in order to keep the patient arm steady and ready for scanning.

At step 1108 the patient's forearm is scanned. In an embodiment, the scan is performed by selecting the patient's name/identification code stored in the database and clicking a 'Scan Patient' button available on a graphical user interface (GUI) running on a computing device coupled with the X-ray apparatus, as described above. FIG. 11D is a screenshot of an exemplary GUI 1170 that may be used to start a scan, in accordance with an embodiment of the present invention. In one embodiment, GUI 1170 includes a "select arm" button 1171, for selection of the dominant or non-dominant arm of the patient. It is usual practice to scan the non-dominant arm of the patient since it is representative of the rest of the bones. Sometimes health professionals may choose to scan the dominant arm of the patient and the apparatus interface allows selection of the dominant or non-dominant arm. Non-dominant arm of the patient is the arm which is not used as often for daily activities. For example, a right-handed person would have the left arm as the non-dominant arm. 'Scan Patient' icon 1172 on GUI 1170 is used to initiate a patient scan, thus the system, in one embodiment, is run from a computer to acquire data being scanned.

In one embodiment, the scan duration is less than five minutes. Double and Quad speed scan modes are available for higher throughput scanning. In various embodiments of the present invention, and as mentioned and described above, the dual energy X-ray apparatus may operate in two configuration modes, namely pencil beam mode and fan beam mode. In the pencil beam configuration mode both horizontal and angular motions of the gantry are required in order to generate a scanned image of the patient's forearm.

The pencil beam scan duration in single speed takes less than 5 minutes. In single speed mode, the pencil beam scans in a first vertical upward motion, moves a fixed distance in the horizontal direction, then scans in a second vertical downward motion. Individual pixel data is gathered in the vertical up and down motion to generate a scan line. Horizontal motion prepares the pencil beam for the next scan line acquisition.

In double and quad speeds, the amount of distance traversed in the horizontal motion per step is increased. This decreases the overall scan time to less than 2.5 minutes for double speed and less than 1.5 minutes for quad speed. In the double and quad speed scanning modes, the horizontal resolution of the scan lines is reduced since the gantry travels a larger horizontal distance per step. This loss in horizontal resolution due to scan line information being spaced apart is compensated by interpolating the scan lines acquired and generating additional scan lines in between the originally scanned lines. Although there is image quality degradation in double and quad speed scans as compared to single speed scans, clinical test results have shown that the accuracy of BMD score drops by about 2% in double speed and by about 4% in quad speed as compared to single speed, resulting in a trade-off between accuracy and patient throughput.

In the fan beam configuration, the vertical motion is eliminated and the scan time is less than 1 minute. Only one scan speed is supported in the fan beam configuration to obtain the highest possible image resolution. In one embodiment, during the scanning process, an X-ray beam passes through the patient's forearm and the attenuated beam illuminates the high-energy and low-energy detectors. Data from the dual energy detectors is gathered in less than 100 micro-seconds of each other to minimize the effect of any patient movement and to maintain the acquisition speed with the gantry movement. To accommodate the side-by-flip-side detector configuration, the horizontal distance traversed by the gantry during a fan beam scan is exactly equal to the distance between the detectors.

Figure 11E:
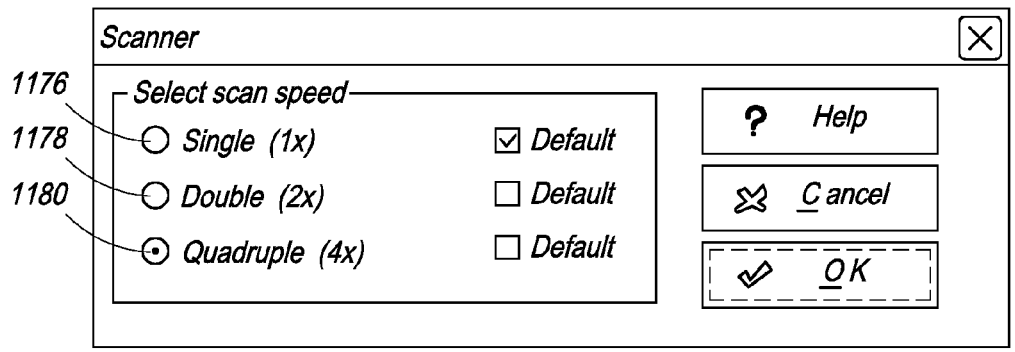
FIG. 11E is a screenshot of an exemplary electronic form that may be used to select scan speed, in accordance with an embodiment of the present invention.

FIG. 11E is a screenshot of an exemplary GUI electronic form that may be used to select scan speed, in accordance with an embodiment of the present invention. Radio buttons 1176, 1178 and 1180 are used to select the scan speed as single, double or quadruple respectively.

Referring back to FIG. 11A, at step 1110 a BMD report is generated by using the scan results. Once the scan is completed, all information is archived into the database and BMD results are calculated and presented to the operator. In various embodiments of the present invention, known algorithms may be used to generate a BMD report by using the scan results. At step 1112 it is determined if a rescan is required. If a rescan is required steps 1104 to 1110 are repeated.

Figure 12:
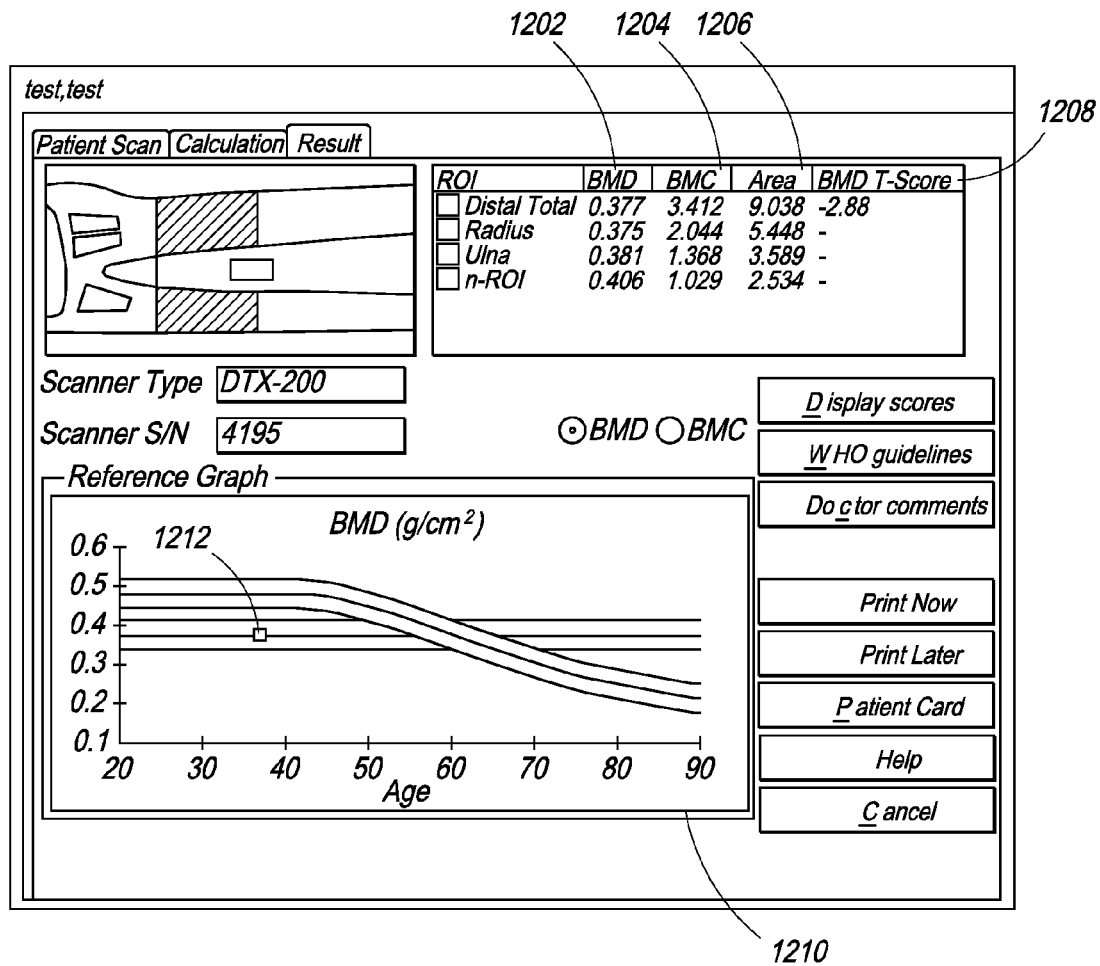
FIG. 12 illustrates an exemplary BMD report which is generated by using the scan results, in accordance with an embodiment of the invention.

FIG. 12 illustrates an exemplary BMD report which is generated by using the scan results, in accordance with an embodiment of the invention. BMD results are listed in a column 1202 entitled 'BMD'. Bone mass content (BMC) results are listed in a column 1204 entitled 'BMC'. Column 1206 lists area calculation results which is the area that is used in the Region of Interest. BMD value is obtained by dividing BMC by Area. Column 1208 lists BMD T-score results. Section 12101110 illustrates reference data obtained from BMD results of patients of same sex and ethnic background. A square marker 1212 is placed within the reference data to illustrate a patient's BMD results as compared to the BMD results of a large sample of scans of patients of similar sex and ethnic backgrounds.

Figure 13A:
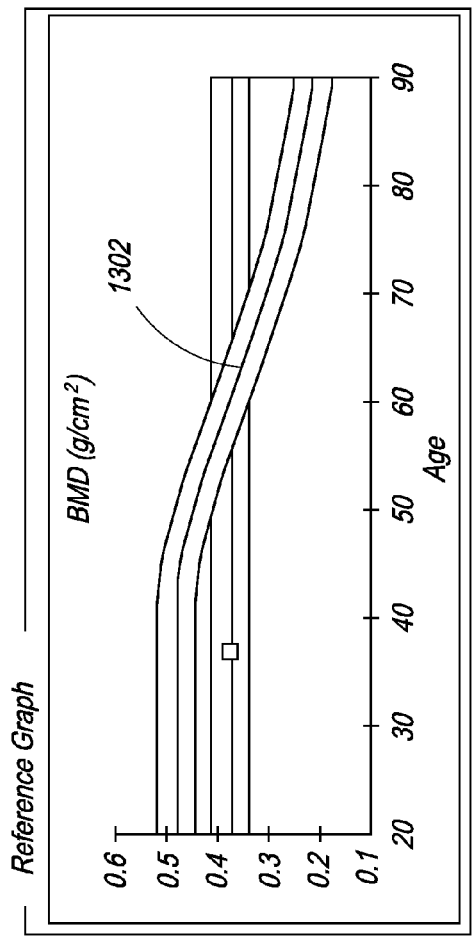
FIG. 13A illustrates a BMD reference graph of females of varying ages.
Figure 13B:
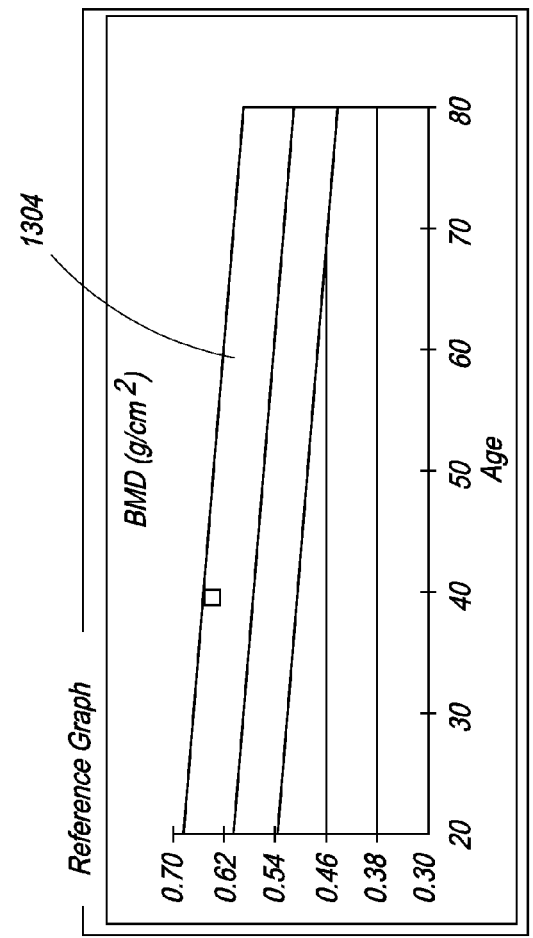
FIG. 13B illustrates a BMD reference graph of males of varying ages.

FIG. 13A illustrates a BMD reference graph of females of varying ages. FIG. 13B illustrates a BMD reference graph of males of varying ages. It is apparent from the graphs that the BMD measurements of women 1302 has a sharp decline in older age, typically after menopause, as compared to BMD measurements of men 1304, where the BMD decline is steady.

Hence, the present invention provides an apparatus and method for measuring bone mass density. The dual energy X-ray apparatus provided by the present invention is easy to use, portable, compact in size, operates on table-top and weighs less than 50 pounds. The apparatus allows all patient information to be pre-loaded in a patient database thereby minimizing the total time the patient spends at the apparatus. The apparatus and method provided by the present invention eliminates the need for repositioning the patient's arm by providing an arm-rest and a holding bar. Further, the present invention provides high resolution images by using detectors having small lateral dimensions spaced closely together which images finer details of the bone and provides sharper edges for accurate, automatic and repeatable determination of the Trapezoidal Region of Interest. In addition, the apparatus utilizes detectors that are less susceptible to radiation damage and provide improved signal-to-noise ratio. Also in order to get accurate measurements, the high energy and low energy acquisitions of any point on the forearm are made within 100 micro-seconds of each other or simultaneously. Yet further, the apparatus and method of the present invention provide for a clutter-free operation using wireless remote mode in which data is transmitted between the apparatus and a computing device using a wireless data link. Yet further, the apparatus is DICOM (Digital Imaging and Communications in Medicine) compatible allowing handling, storing, printing, and transmitting of patient information, scan image and scan results in a standard format.

Figure 14:
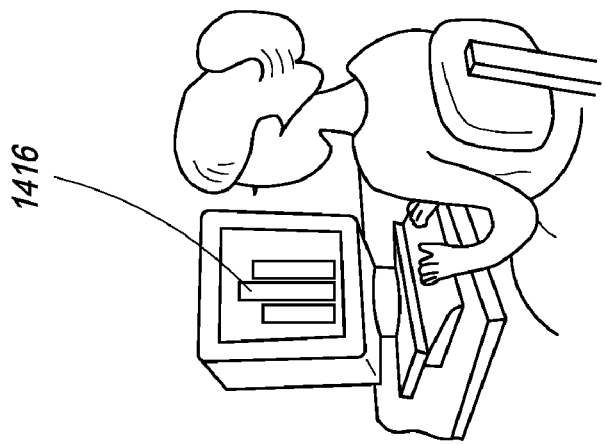
FIG. 14 illustrates wireless configuration of the dual energy X-ray apparatus, in accordance with an embodiment of the present invention.
Figure 14:
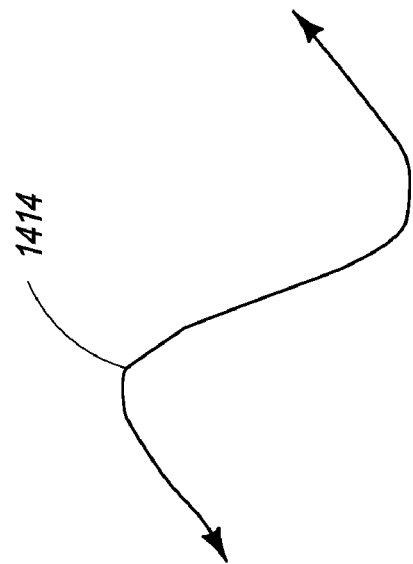
Figure 14:
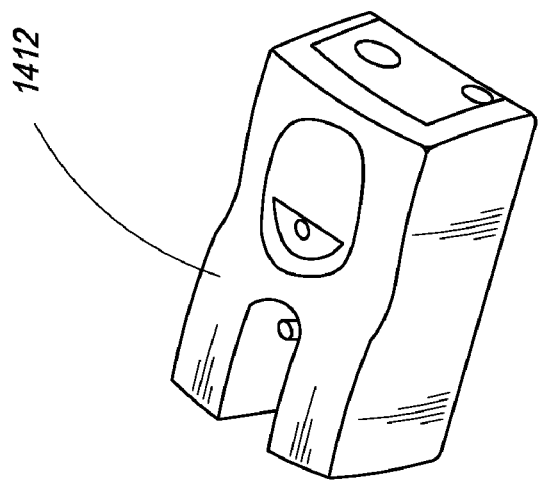

In an embodiment, the scan image, data analysis and report computer is connected directly to the dual energy X-ray apparatus and placed next to the apparatus. In another embodiment, to minimize clutter around the scanning apparatus, the data analysis computer is placed remotely and communicates with the scanning apparatus through a wireless connection. FIG. 14 illustrates wireless configuration of the dual energy X-ray apparatus, in accordance with an embodiment of the present invention. X-ray apparatus 1412 is connected to computing device 1414 via wireless medium 1416.

Various safety features are provided in the dual energy X-ray apparatus. In an embodiment of the present invention, a buzzer is activated for a short duration of time, e.g. three seconds prior to turning on the X-rays and initiating a scan. During emission of X-rays from the apparatus, an LED indicator provided on the apparatus is turned on and also a predefined radiation icon is displayed on a computer screen coupled with the apparatus, thereby indicating that X-rays are being emitted. An emergency stop button is provided on the apparatus to turn off all power to the apparatus in case of any emergency.

While the exemplary embodiments of the present invention are described and illustrated herein, it will be appreciated that they are merely illustrative. It will be understood by those skilled in the art that various changes in form and detail may be made therein without departing from or offending the spirit and scope of the appended claims.

We claim:

1. An X-ray apparatus for measuring a patient's bone density, comprising:
 a gantry having a base, a first end, and a second end, further comprising:
  a radiation source configured to direct radiation through said first end, wherein said radiation source comprises a mono-energetic generator producing radiation at a first energy, and
  a dual energy detector array located in said second end, comprising at least one detector element pair which comprises at least one high energy detector element and at least one low energy detector element that are arranged in a post-collimated stack configuration, wherein the post-collimated stack configuration comprises a metal strip placed underneath the low energy detector element and above the high energy detector element, a first metal piece for post-collimation positioned adjacent to the high energy detector element to reduce scatter radiation from entering into the high energy detector from a first side and a second metal piece for post-collimation positioned adjacent to the high energy detector element to reduce scatter radiation from entering into the high energy detector from a second side, wherein both said first metal piece and second metal piece are positioned in planes parallel to said high energy detector element and substantially perpendicular to said metal strip;
 an armrest area, further comprising a holding bar, for positioning a patient's forearm in the apparatus wherein said armrest area is positioned between said first end and said second end; and
 a computing system, further comprising a monitor having a display, wherein said display further comprises a graphical user interface (GUI) for controlling said apparatus.

2. The apparatus of claim 1 wherein the first energy is 55 KeV and has a current of 0.3 mA.

3. The apparatus of claim 1 wherein the radiation source is collimated to provide a pencil beam of X-rays.

4. The apparatus of claim 1 wherein the radiation source is collimated to provide a fan beam of X-rays.

5. The apparatus of claim 1 wherein the at least one detector element pair comprises a low energy detector element and a high energy detector element arranged in a side-by-flip side configuration.

6. The apparatus of claim 5 wherein the side-by-flip side configuration comprises a low energy detector element, having a top side and a back side, and a high energy detector element, having a top side and a back side, placed adjacent to each other wherein the low energy detector element is placed with its top side up and wherein the high energy element is placed with its back side up.

7. The apparatus of claim 1 wherein the at least one detector element pair comprises a low energy detector element and a high energy detector element arranged in a post-collimated stack configuration.

8. The apparatus of claim 1 wherein the gantry is capable of moving horizontally and vertically.

9. The apparatus of claim 1 further comprising at least one optical sensor for detecting the position of the gantry.

10. The apparatus of claim 1 wherein the gantry is pivotally attached to a housing and wherein the pivotable attachment permits the first end and second end of the gantry to move in an angular motion around the armrest area.

11. An X-ray apparatus for measuring a patient's bone density, comprising:
 a gantry having a base pivotally attached to a housing, a first end, and a second end, wherein said first end and second end have a first alignment, further comprising:
  a radiation source configured to direct radiation through said first end, wherein said radiation source comprises a mono-energetic generator producing radiation at a first energy, and
  a dual energy detector array located in said second end, comprising at least one detector element pair which comprises at least one high energy detector element and at least one low energy detector element that are arranged in a post-collimated stack configuration, wherein the post-collimated stack configuration comprises a metal strip placed underneath the low energy detector element and above the high energy detector element, a first metal piece for post-collimation positioned adjacent to the high energy detector element to reduce scatter radiation from entering into the high energy detector from a first side and a second metal piece for post-collimation positioned adjacent to the high energy detector element to reduce scatter radiation from entering into the high energy detector from a second side, wherein both said first metal piece and second metal piece are positioned in planes parallel to said high energy detector element and substantially perpendicular to said metal strip;
 an armrest area, further comprising a holding bar, for positioning a patient's forearm in the apparatus wherein said armrest area is positioned between said first end and said second end; and
 a computing system, further comprising a monitor having a display, wherein said display further comprises a graphical user interface (GUI) for controlling said apparatus.

12. The apparatus of claim 1 wherein the first end and second end are configured to move in an angular motion around the armrest area while maintaining said first alignment.

13. The apparatus of claim 1 wherein the radiation source is collimated to provide at least one of a pencil beam of X-rays or a fan beam of X-rays through said first end.

* * * * *